United States Patent
Meier et al.

(10) Patent No.: US 9,126,346 B2
(45) Date of Patent: Sep. 8, 2015

(54) BODY CARE DEVICE

(75) Inventors: Hanspeter Meier, Langenthal (CH); Franz Fischer, Triengen (CH); Kevin Barry, Fairfield, CT (US); Kelvin Stewart, Milford, CT (US); Todd Zeigher, Trumbult, CT (US)

(73) Assignees: TRISA HOLDING AG, Triengen (CH); EVEREADY BATTERY COMPANY INC., Saint Louis, MO (US)

( * ) Notice: Subject to any disclaimer, the term of this patent is extended or adjusted under 35 U.S.C. 154(b) by 802 days.

(21) Appl. No.: 13/144,855

(22) PCT Filed: Feb. 12, 2010

(86) PCT No.: PCT/EP2010/000894
§ 371 (c)(1),
(2), (4) Date: Sep. 14, 2011

(87) PCT Pub. No.: WO2010/091882
PCT Pub. Date: Aug. 19, 2010

(65) Prior Publication Data
US 2011/0314677 A1    Dec. 29, 2011

(30) Foreign Application Priority Data
Feb. 13, 2009   (EP) .................................... 09002342

(51) Int. Cl.
*B26B 21/52*   (2006.01)
*A46B 5/00*    (2006.01)
(Continued)

(52) U.S. Cl.
CPC ............... *B26B 21/526* (2013.01); *A46B 5/007* (2013.01); *A46B 5/0062* (2013.01); *A46B 13/02* (2013.01);
(Continued)

(58) Field of Classification Search
CPC .... A61C 17/16; A61C 17/221; A61C 17/222; A61C 17/225; B26B 21/40; B26B 21/405; B26B 21/4062; B26B 21/4056; B26B 21/522; B26B 21/526; A46B 9/021; A46B 9/04; A46B 15/0002; A46B 2200/1066; A46B 2200/106; A46B 2200/1053
USPC ............ 30/34.05, 41.7, 41.8, 47–51; 15/22.1, 15/105, 167.1; 132/218; 401/126, 129
See application file for complete search history.

(56) References Cited

U.S. PATENT DOCUMENTS 4,253,212 A * 3/1981 Fujita ........................... 15/167.1
4,450,599 A   5/1984 Scheller et al.
(Continued)

FOREIGN PATENT DOCUMENTS

DE           40 12 413 A1    10/1991
DE    10 2005 008 199 A1     8/2006
(Continued)

OTHER PUBLICATIONS

International Search Report issued in International Application No. PCT/EP2010/000894 on Jun. 7, 2010.
(Continued)

*Primary Examiner* — Jason Daniel Prone
(74) *Attorney, Agent, or Firm* — Oliff PLC

(57) ABSTRACT

The inventive body care device having a handle and a treatment head, which is hingedly connected mechanically therewith, has a flexible zone for enabling an elastic deflection of the treatment head with respect to the handle and a deflection sensor, which is capable of generating an electric signal as a function of the elastic deflection. This signal can be used to control an automatic start and/or stop function, a use counter and/or operating states of an electric vibrational element integrated in the body care device.

23 Claims, 9 Drawing Sheets

(51) Int. Cl.

| | | |
|---|---|---|
| *A46B 13/02* | (2006.01) | |
| *A46B 15/00* | (2006.01) | |
| *A61C 17/22* | (2006.01) | |
| *A61C 17/34* | (2006.01) | |
| *B26B 21/40* | (2006.01) | |

(52) U.S. Cl.
CPC ........... *A46B 13/023* (2013.01); *A46B 15/0002* (2013.01); *A46B 15/0012* (2013.01); *A61C 17/221* (2013.01); *A61C 17/3481* (2013.01); *B26B 21/4056* (2013.01); *B26B 21/528* (2013.01); *A46B 2200/1053* (2013.01); *A46B 2200/1066* (2013.01)

(56) References Cited

U.S. PATENT DOCUMENTS

| | | | |
|---|---|---|---|
| 5,282,291 | A | 2/1994 | Spieler et al. |
| 5,299,354 | A | 4/1994 | Metcalf et al. |
| 5,671,535 | A | 9/1997 | Van Der Borst et al. |
| 5,678,316 | A | 10/1997 | Althaus et al. |
| 5,784,742 | A * | 7/1998 | Giuliani et al. .............. 15/22.1 |
| 6,009,623 | A * | 1/2000 | Orloff ............................ 30/41.7 |
| 6,092,252 | A | 7/2000 | Fischer et al. |
| 6,327,734 | B1 * | 12/2001 | Meginniss et al. ............. 15/105 |
| 7,049,790 | B2 | 5/2006 | Pfenniger et al. |
| 7,240,390 | B2 | 7/2007 | Pfenniger et al. |
| 7,241,413 | B2 | 7/2007 | Pfenniger et al. |
| 7,383,603 | B2 * | 6/2008 | Edwards ....................... 15/167.1 |
| 7,409,767 | B2 | 8/2008 | Dombrowski et al. |
| 7,526,828 | B2 | 5/2009 | Kniese |
| 7,713,461 | B2 | 5/2010 | Pfenniger et al. |
| 7,721,371 | B2 | 5/2010 | Pfenniger et al. |
| 7,748,069 | B2 | 7/2010 | Dawley |
| 7,905,020 | B2 | 3/2011 | Rozenkranc |
| 7,913,392 | B2 | 3/2011 | Rozenkranc |
| 2004/0098862 | A1 * | 5/2004 | Orloff ............................ 30/41.7 |
| 2005/0172493 | A1 | 8/2005 | Fischer et al. |
| 2006/0032512 | A1 | 2/2006 | Kress et al. |
| 2009/0070947 | A1 | 3/2009 | Baertschi et al. |
| 2010/0175207 | A1 * | 7/2010 | Kraus et al. ..................... 15/22.1 |
| 2010/0319145 | A1 | 12/2010 | Neyer et al. |
| 2010/0325828 | A1 * | 12/2010 | Braun et al. .................. 15/167.1 |
| 2013/0239349 | A1 * | 9/2013 | Knights et al. ............... 15/167.1 |
| 2013/0247321 | A1 * | 9/2013 | Sichau ......................... 15/167.1 |
| 2014/0165311 | A1 * | 6/2014 | Donegan ....................... 15/22.1 |

FOREIGN PATENT DOCUMENTS

| | | |
|---|---|---|
| DE | 10 2006 057 492 A1 | 6/2008 |
| EP | 1 531 030 A2 | 5/2005 |
| EP | 2218559 A1 * | 8/2010 |
| EP | 2396150 B1 * | 11/2014 |
| JP | A-5-329024 | 12/1993 |
| WO | WO 9202159 A1 * | 2/1992 |
| WO | WO 92/10979 A1 | 7/1992 |
| WO | WO 99/03372 A1 | 1/1999 |
| WO | WO 2004/018161 A2 | 3/2004 |
| WO | WO 2004/030891 A1 | 4/2004 |
| WO | WO 2005/046508 A1 | 5/2005 |
| WO | WO 2005/077616 A1 | 8/2005 |
| WO | WO 2006/037358 A1 | 4/2006 |
| WO | WO 2007/029163 A2 | 3/2007 |
| WO | WO 2007/107274 A1 | 9/2007 |
| WO | WO 2008/060482 A2 | 5/2008 |
| WO | WO 2010091882 A1 * | 8/2010 |

OTHER PUBLICATIONS

Written Opinion of the International Searching Authority issued in International Application No. PCT/EP2010/000894 on Jun. 7, 2010.
International Preliminary Report on Patentability issued in International Application No. PCT/EP2010/000894 on Aug. 16, 2011.

* cited by examiner

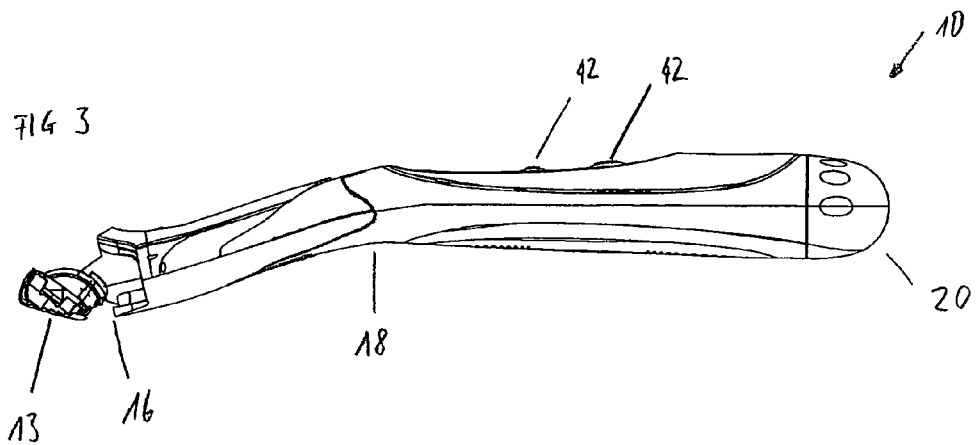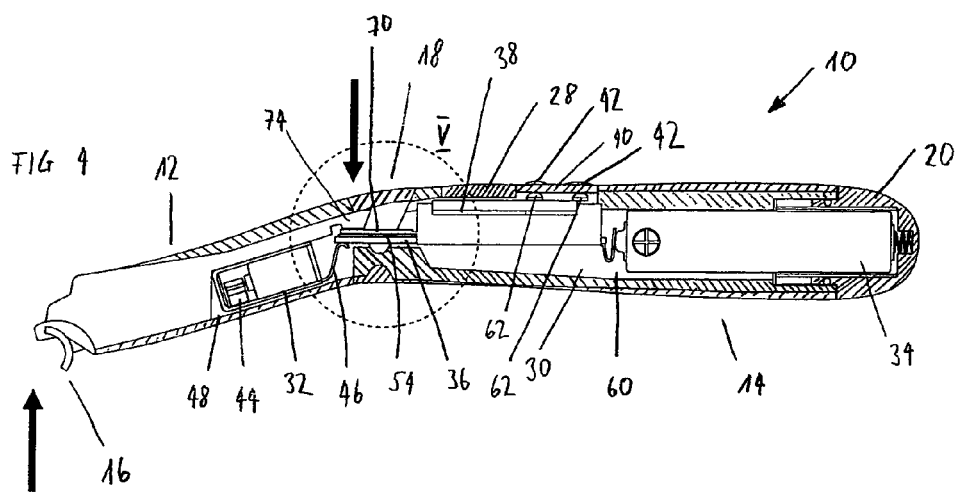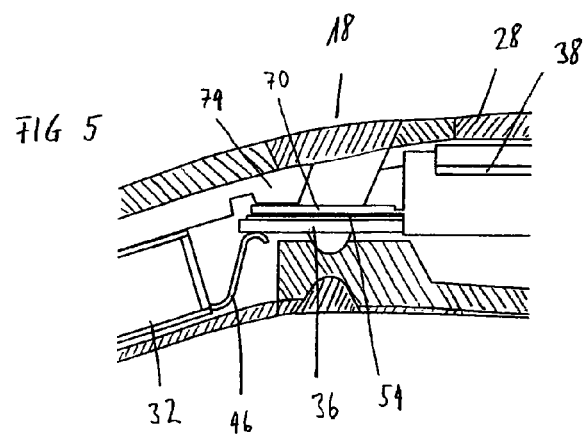

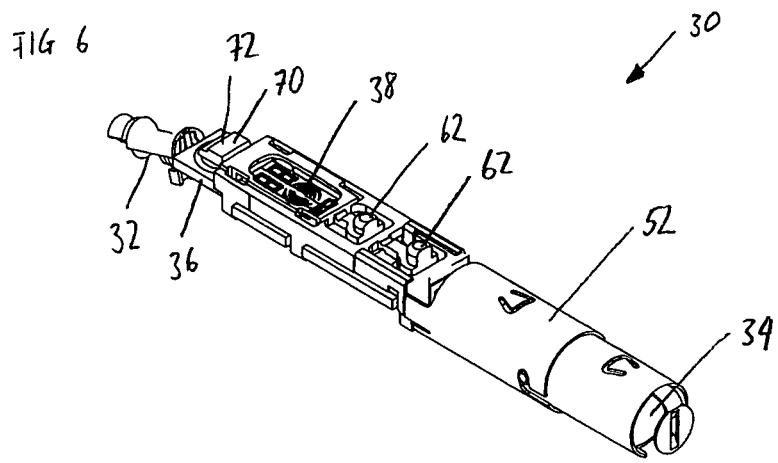
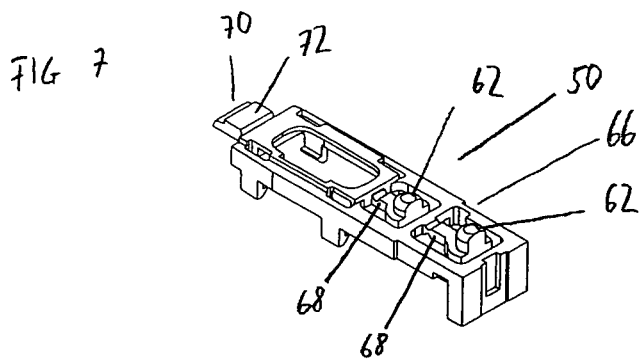
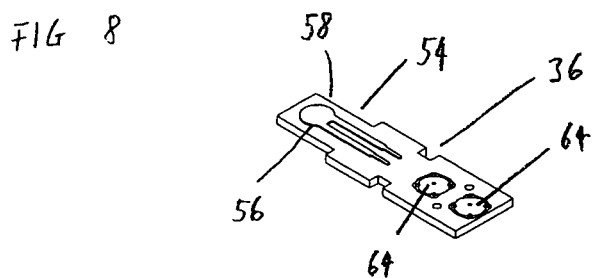
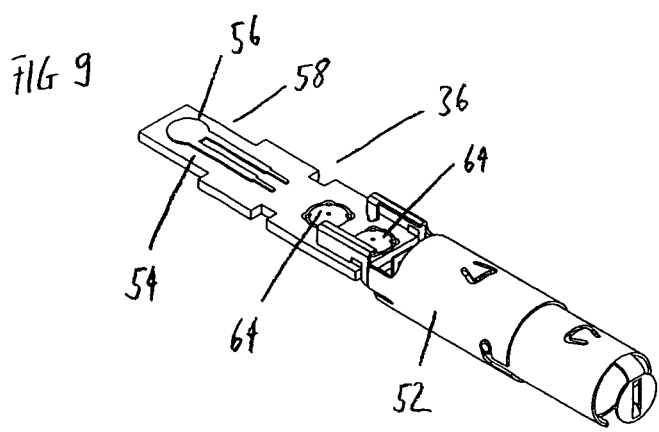

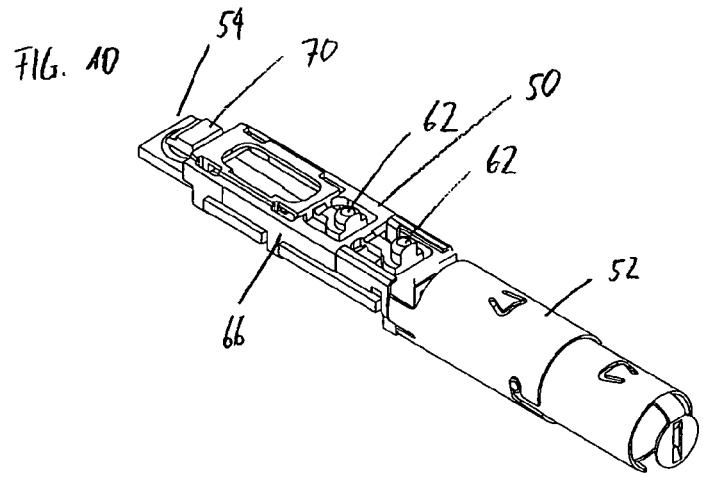
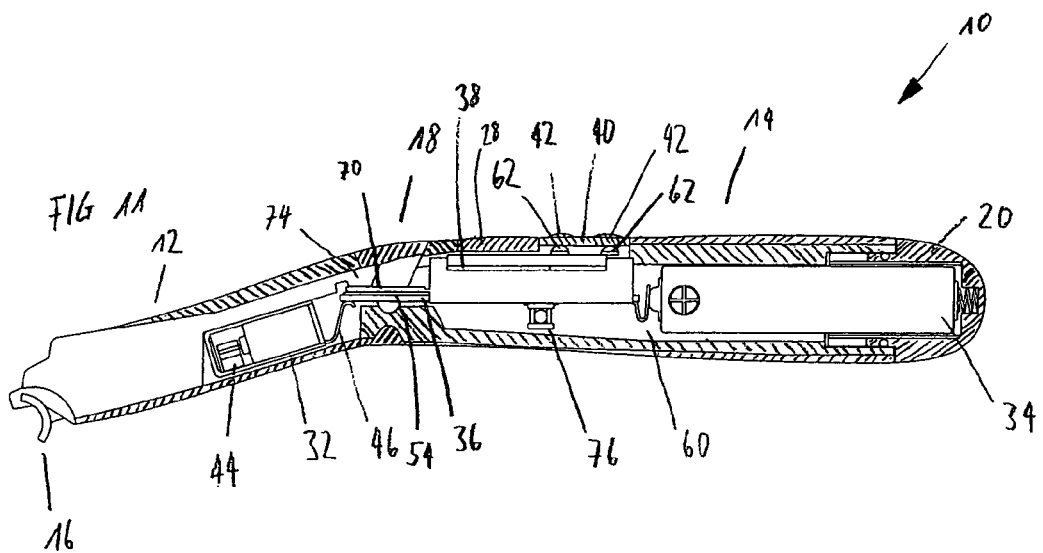
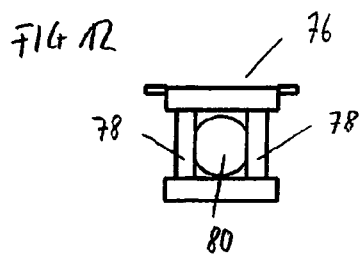
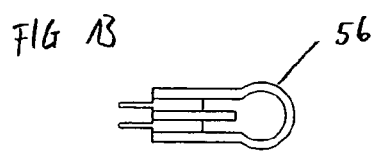

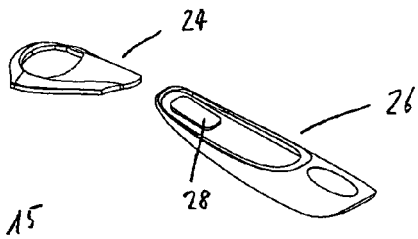
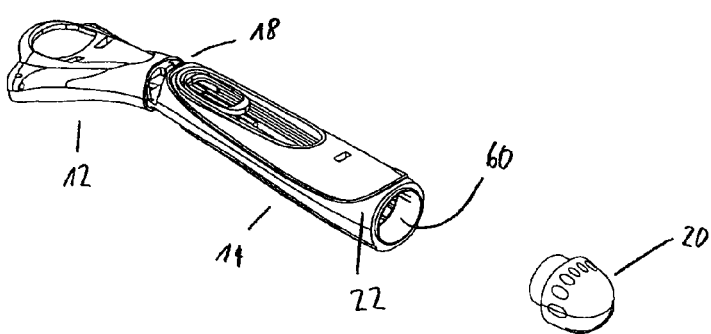
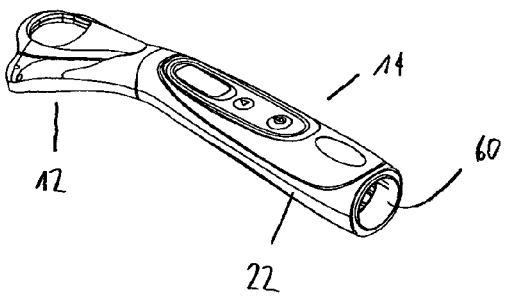
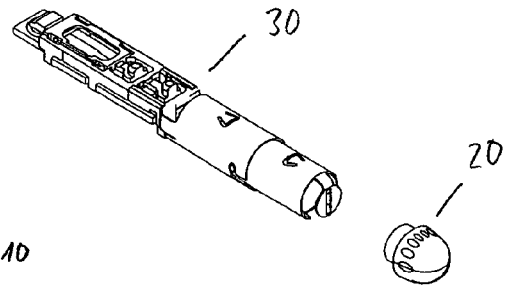
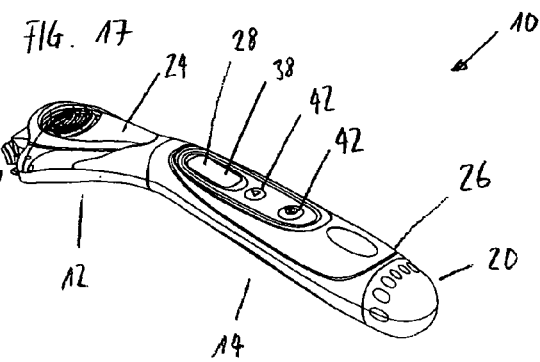

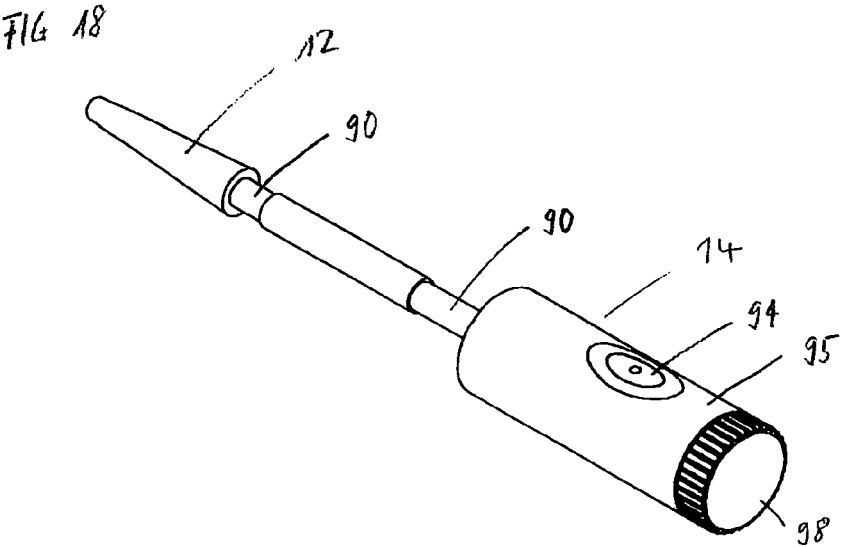
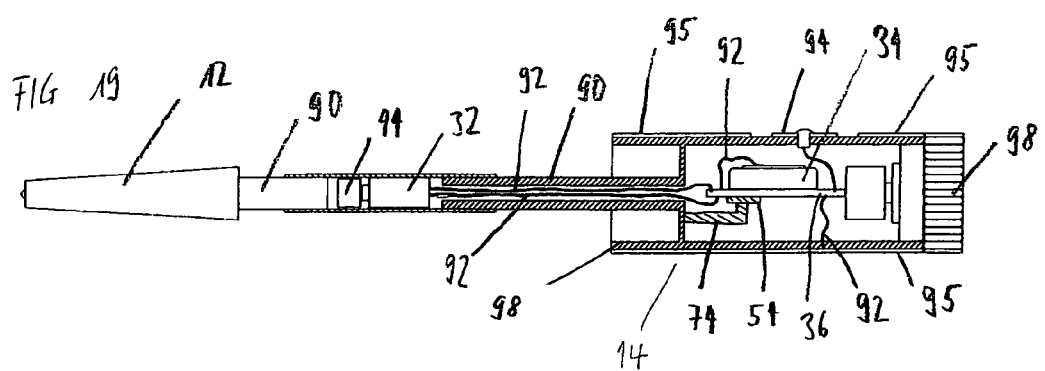

BODY CARE DEVICE

The present application is a national stage application of PCT/EP2010/000894, filed Feb. 12, 2010, which in turn claims priority to EP 09002342.5 filed Feb. 13, 2009, the disclosures of each of which are hereby incorporated by reference in their entireties.

BACKGROUND

The present invention relates to a body care device such as a wet razor, a toothbrush or a mascara applicator of the introductory portion of claim 1 and a method for the production thereof according to claim 23.

Body care devices such as wet razors are generally known devices for personal hygiene. Body care devices such as wet razors may be equipped with an electrically operated vibrating element, by means of which easier cutting of hairs is made possible by a transfer of certain vibrations to razor blades disposed in a razor cartridge or razor head.

A wet razor is disclosed, for example, in WO 2007/029163. The wet razor, described therein, has a vibrational element, which is supplied with electricity, and is equipped with a resettable use indicator.

A further wet razor is known from WO 2005/077616. This wet razor has a body with a handle region, a thereon adjoining neck region and a head region, which is disposed at the neck region opposite to the handle region. An electrical vibrational device and a device for supplying electricity to the vibrating device are disposed in the interior of the body, which is produced by injection molding.

A wet razor, which is equipped with an electric vibrating element, is also disclosed in WO 2006/037358. In addition, the wet razor is equipped with a control circuit for adjusting the frequency of the vibrating element.

SUMMARY

It is an object of the present invention to provide a body care device, preferably a wet razor, which is particularly comfortable to handle.

This objective is accomplished by a body care device of claim 1. Particularly preferred embodiments are equipped with the distinguishing features listed in the dependent claims.

The inventive body care device has a handle and a treatment head, which is mechanically connected therewith. The treatment head of a body care device such as a wet razor can include, for example, a razor cartridge having an arrangement of razor blades, can be deflected elastically with respect to the handle because of a flexible zone. Moreover, the body care device has a deflection sensor, which is capable of generating an electric signal as a function of this elastic deflection.

This electric signal may be used, for example, for switching the inventive body care device on and off automatically, for the force-dependent adjustment of the vibration speed, for counting the number of uses as well as for changes in the operating state in general and results in the advantages that it is possible to do without the switching on and off by hand, to adapt the vibrational speed optimally to the force with which the razor contacts the skin, to give the user an indication of the need to change, for example, the razor cartridge and, since a mechanical switching on and off is no longer necessary in principle, to avoid a therefore possible leakage problem with respect to the penetration of water.

The properties and functions previously mentioned of the inventive body care device, including the details listed in the following, can also be used in other body care devices. For this purpose, the treatment head can be provided with other attachments, preferably with arrangements of bristles and optionally to be adapted in a known manner in its external shape. By these means, appropriate electric toothbrushes with oscillating, swiveling or translatory brush movements, vibrational or sonic tooth brushes, electric toothbrushes with combined movements of one or more cleaning elements, mascara products or mascara applicators for the application of mascara, massage equipment, equipment for body hair removal, applicators for the application of cosmetic products, etc. can be constructed with in the sense of the present invention. In order to avoid repetitions in the description that follows, a detailed individual presentation of the configuration of these products is omitted. It is, however, pointed out explicitly that the variational configurations of the Figures described can be employed with minor structural adaptations analogously also for all the body care devices mentioned above, without leaving the scope of this invention.

BRIEF DESCRIPTION OF THE DRAWINGS

A particularly preferred embodiment is described in detail in the following, using the inventive body care device in the form of a wet razor as an example, by means of the drawings, in which, diagrammatically and in detail, FIG. 3 shows a plan view of the wet razor, shown in FIGS. 1 and 2, with the razor cartridge mounted, FIG. 4 shows a longitudinal, sectional representation of the wet razor, shown in FIGS. 1, 2 and 3, with an electric vibrating element, which is supplied via an energy storage system, mounted in the handle of the wet razor, and mounted the in the treatment head, once again showing the razor cartridge, FIG. 5 shows a detailed view of the section V from the longitudinal sectional representation in FIG. 4, FIG. 6 shows a perspective representation of an electrical functional unit of the wet razor shown in FIGS. 1 to 4, FIG. 7 shows a perspective view of a first holding element of the electrical functional unit shown in FIG. 6

FIG. 8 shows a perspective representation of a circuit board, on which a force-sensitive resistance (FSR) is fastened, FIG. 9 shows a perspective representation of a unit of the electrical functional unit, without the first holding element shown in FIG. 7 and without the electrical vibrating element visible in FIG. 6, FIG. 10 shows a perspective representation of the unit, shown in FIG. 9, with the installed first holding element shown in FIG. 7, FIG. 11 shows a diagrammatic longitudinal sectional representation of a further embodiment of the inventive wet razor, for which additionally a movement sensor is disposed on the circuit board, FIG. 12 shows a side view of the movement sensor, which can be seen in FIG. 11, FIG. 13 shows a plan view of the force-sensitive resistance (FSR) of a deflection sensor of the inventive wet razor, FIG. 14 shows a perspective representation of a first shell part and of a second shell part, which are provided on the upper side of the inventive wet razor, the second shell part being shown positionally with a window, FIG. 15 shows a perspective representation of a basic body of a hard material, including an end cap, FIG. 16 shows a perspective representation of the basic body, which is shown in FIG. 15, on the upper side of which the shell parts are fastened, which are shown already in FIG. 14 and are provided with an additional material component, as well as the unit shown in FIG. 10 before the latter is installed, and an end cap;

FIG. 17 shows a perspective representation of the finished wet razor, including a cartridge loading mechanism at the treatment head for accommodating a razor cartridge, FIG. 18 shows a perspective view of an inventive mascara brush, FIG. 19 shows a representation of a longitudinal section through the mascara brush shown in FIG. 18

DETAILED DESCRIPTION

Figure 1:
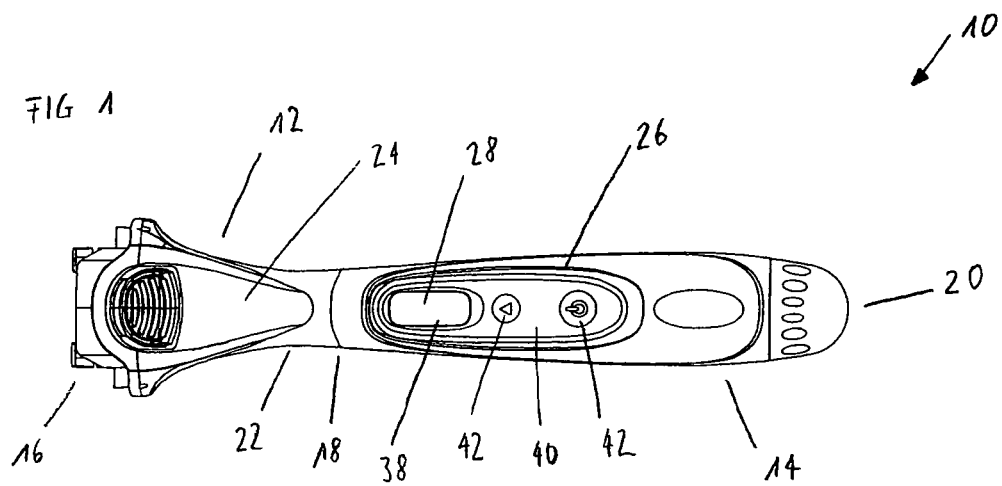
FIG. 1 shows a plan view of an upper side of the inventive wet razor with a treatment head for accommodating an exchangeable razor cartridge, which is not shown.
Figure 2:
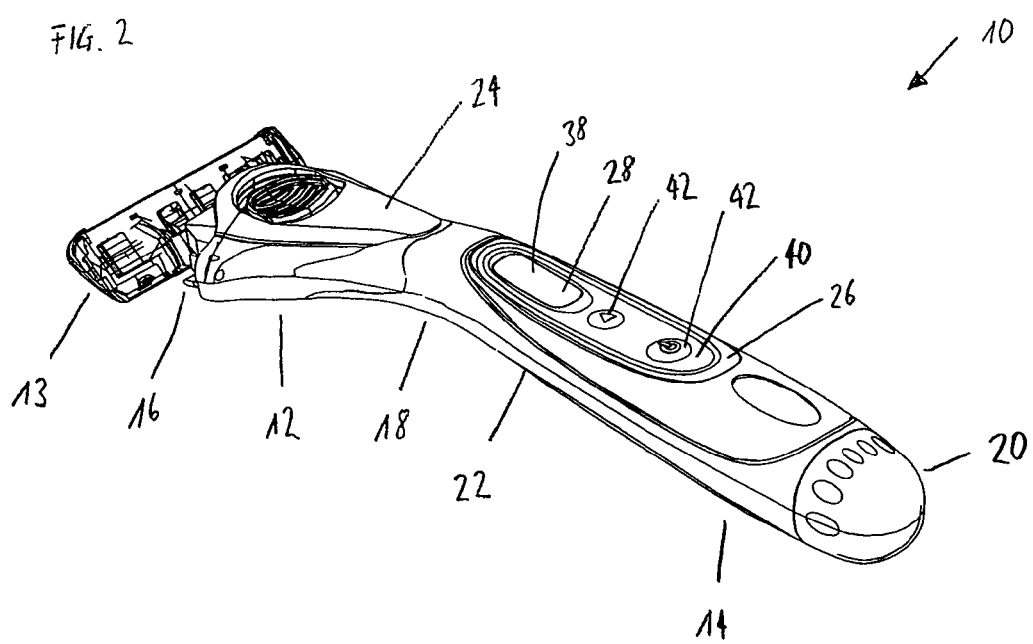
FIG. 2 shows a perspective view of the wet razor, shown in FIG. 1, with the exchangeable razor cartridge mounted.

The inventive body care device 10 in the form of a wet razor, shown in FIGS. 1 and 2, has a treatment head 12 and thereon an adjoining handle 14. The treatment head 12 is equipped with a cartridge holding mechanism 16 for the user selectable accommodation of a razor cartridge. Other body care devices may have correspondingly other attachments or applicators at this place. Moreover, the attachments or applicators may be fixed in place or can be exchangeable. The treatment head 12, which can taper to the handle, is hingedly mechanically connected with the handle 14 in a discrete flexible zone 18. In some embodiments the treatment head 12 is mechanically connected with the handle 14 by a thin bridge or film hinge. Preferably the treatment head 12 is integrally formed with the handle 14. In other embodiments the treatment head 12 and the handle 14 can be separate components parts joined by the thin bridge which can be a further separate part or which can be integrally formed with the treatment head 12 or the handle 14. In further embodiments the treatment head 12 is mechanically connected with the handle 12 by a hinge joint. As a result, an elastic deflection of the treatment head 12 with respect to the handle 14, which, when held in the hand of a user during normal use, becomes possible. In the free end region of the handle 14, an end cap 20 is removable and re-installable.

In some embodiments the wet razor 10 is built up on a basic body 22 of a hard material (e.g. hard plastic). As hard material, plastic components such as polypropylene (PP), polyester (PET), polycyclohexanedimethanol terephthalate (PCT/PCT-A (acid-modified/PCC-G (glycol modified)), polyethylene (PE), polystyrene (EPS), such as, for example, BDS Karesin, styrene acrylonitrile (SAN), polymethyl methacrylate (PMMA), acrylobutadiene styrene (ABS), polyoxymethylene (POM), polyamide (PA), etc., preferably polypropylene (PP) is used. In other embodiments described later, preferred hard materials can include metals, e.g. die-cast zinc alloy.

The basic body 22 may, however, have or be molded to one or more regions of a soft material. As soft materials, plastics, such as low density polyethylene (PE-LD), a high density polyethylene (PE-HD), polyethylene (PE), polyvinyl chloride (PVC), rubber elastic materials such as a polyurethane (PUR), a thermoplastic elastomer (TPE), a polyolefin-based elastomer, etc. are used, a thermoplastic elastomer (TPE) being preferred. The Shore A hardness of the soft material preferably is below 90 and, particularly, below 50.

In the transition region between the treatment head 12 and the handle 14, the basic body 22 of hard material is equipped with a recess, which can be U- or V-shaped in cross section, on the upper side and/or the lower side of the bridge or film hinge. Optionally, it is possible to supplement the recesses with a stop, which appropriately limits the maximum deflection of the treatment head 12 with respect to the handle 14 and prevents excessive elongation of the flexible zone 18. The recess is at least partially filled with the soft material.

The flexibility of the flexible zone 18 is adjusted by the interaction of hard and soft materials. In this connection, the modulus of elasticity of the hard material and the Shore A hardness of the soft material play a significant role. The basic body 22 consists of a coherent structure of hard material, which comprises the treatment head 12 and the handle 14. The flexible zone 18 between the treatment head 12 and the handle 14 has a thin bridge or a film hinge of hard material. The flexibility of the flexible zone 18 can also be adjusted by the dimensions of this bridge. While shaving, many forces are exerted on the treatment head 12 that include a component of the combined forces directed generally perpendicularly to the longitudinal direction of the handle 14. This force causes the treatment head to be rotated about the flexible zone 18 or the bridge or the film hinge of hard material. With that, an opposing force is exerted on a deflection sensor 54, which will be described in the following, through an actuating extension 74, which will also be explained later.

Because of the deflection of the treatment head 32 about the bridge or the film hinge, the soft material is compressed on one side and extended on the other side. In order to be able to withstand these different stresses, it is proposed that the side of the flexible zone, which consists of soft material and is stressed by extension, be configured in a more massive fashion than the zone 18, which is intended to be compressed, and may be constructed as a thin membrane with a thickness of less than 3 mm and preferably of less than 1.5 mm. The side of the flexible zone 18, consisting of soft material, must have a sufficient "reservoir of material" with a thickness of more than 1.5 mm and preferably of more than 3 mm, in order to be able to withstand the extension.

The flexible zone 18 is formed adjacent an end region of a hollow cavity for accommodating an electrical functional unit 30. This is necessary, since the movement of the actuating extension 74, initiated by the flexibility, interacts directly or indirectly with the electric functional unit 30, particularly the deflection sensor 54.

In other embodiments, the basic body 22 can comprise more than one component part. For example, the handle 14 and treatment head 12 can be separate component parts joined at a mechanical hinge therebetween, the hinge providing another discrete flexible zone 18 by permitting deflection of the treatment head 12 relative to the handle 14 about an axis of the hinge. An elastic part such as a metal spring, e.g. a compression or torsion spring is provided adjacent the hinge to provide the previously discussed elastic deflection of the treatment head 12 with respect to the handle 14. The region of the wet razor near the flexible zone can be encased in a flexible thin-walled sleeve for aesthetic or decorative reasons. In this embodiment materials other than the hard plastic materials previously mentioned can be employed for one or both the handle 14 and treatment head 12, e.g. die-cast zinc alloy.

Decorative elements, such as a first shell part 24, shown in FIG. 14, and a second shell part 26 of a hard material, may be mounted, for example, on the upper side of the basic body is shown in FIG. 1. One or more shell parts may also be mounted on the upper side, laterally or on the underside. The hard material used for this purpose may be transparent, for example, for forming a window 28 disposed at the second shell part 26, transparent, translucent or opaque. Before they are mounted on the basic body 22, the decorative elements of hard material can be finished or decorated, for example, by galvanizing or sputtering, by being coated physically or chemically (PVD, CVD), by being painted or printed, by having films embossed hot or cold, by transfer films, etc.

As is evident, for example, from the sectional representation of FIG. 4, the basic body 22 has a series of recesses. For example, a recess is provided in the region of the treatment head 12 for the razor cartridge holding mechanism 16 as well as a hollow cavity for the electrical functional unit 30, which is shown in FIG. 6. With regard to the latter, the basic body 22 has cavities for an electric vibrating element 32, an energy storage device 34, which is provided for supplying energy to the vibrating element 32, as well as a circuit board 36, which is connected electrically with both. In this connection, it should be noted that the cavity for the electric vibrating element 32 may also be displaced together with the latter further in the direction of the free end region of the treatment head 12 or also further in the direction of the handle 14. Moreover, the already mentioned window 28 for making visible, for example, a display unit underneath, which is shown, for example, in FIG. 6, may be formed directly in the basic body 22 from a transparent or translucent hard or soft material.

While shaving, a component of the combined many shaving forces is exerted generally perpendicularly to the longitudinal direction of the handle 14 onto the treatment head 12. This force brings about a deflection of the treatment head 12 about the flexible zone 18 or the bridge or the film hinge of hard material. With that, a force is produced in the opposite direction by means of the actuating extension 74 on the force element 70 and, from there, on the deflection sensor 54 or the force-sensitive resistance. By means of arrows, FIG. 4 shows how the forces act.

The already mentioned recesses in the interior of the basic body 22 ensure not only that the electrical functional unit 30 is accommodated but also, at the same time, that it is held and positioned in the basic body 22.

The window 28, which enables visual information to be exchanged from the display unit 38, disposed in the interior of the basic body 22, to the user, is connected permanently with the basic body 22 by means of injecting a hard or soft material, for example, in a multi-component injection molding process at least partially over it, by means of a positive connection, a frictional connection, by fusion joining or by (ultrasonic) welding, gluing, etc. An outer surface of a welding edge, which may be formed thereby, preferably lies in a plane with the outer surface of the basic body 22. The same method of connection can be used for the already described decoration elements, for example, for the shell parts 24, 26.

The window 28 preferably has an almost rectangular shape with rounded corners and is adapted appropriately to the display unit 38 below. This form is used particularly for display units 38 in the configuration of an LCD (liquid crystal display) or an OLED display. In the event that some light emitting diodes (LED) are used alternatively or additionally as display unit 38, the window 28 can also be formed to be very narrow, for example, so as to follow a surface contour or a line separating two different materials or geometries. The window 28 has a material thickness of 0.5 mm to 4 mm and preferably of 0.7 mm to 2 mm. For optically increasing or decreasing the appearance of the display unit 38 below, the outer and/or the inner surface of the window 28 may at least sectionally be configured with a concave or convex surface contour to provide a lens. The window may also, of course, be disposed on the opposite underside or side surfaces.

As is evident from FIG. 4, a soft material preferably fills the recesses in the region of the flexible zone 18. By these means, it is ensured that the deflection occurring in this region can be limited and that, after an elastic deflection, the treatment head 12 can return into its original position; in other words, a restoration of the position of the treatment head 12 with respect to the handle 14 is additionally provided. The attachment of soft material to the basic body 22 furthermore improves the haptics of the handle 14, seals the already mentioned cavity for the electrical functional unit 30, for example, in the free end region of the handle 14 at the contact place to the end cap 20 and embeds and anchors elements of a hard material, such as, for example, the window 28, the lid 48, any decorative parts, the first and/or second shell parts 24, 26 etc. at the basic body 22. Moreover, a switching membrane 40 of a soft material may be formed above electrical switching elements 42. Soft material is also used in damping zones, on the one hand, to prevent transfer of vibrations from the treatment head 12 to the handle 14 and, on the other, for the damped mounting of further elements, such as the electrical functional unit 30 or the energy storage system 34, for preventing vibrational noise and for taking up tolerances. In this connection, preferably the same soft material is used for the different function areas. These areas are then preferably formed coherently by means of passages and/or connecting channels molded in the basic body 22 and, during the manufacture, can be formed by a single injection point in an injection molding process. Alternatively, it is, of course, also possible to use different materials, preferably with different Shore A hardnesses, which are integrally molded at several injection points.

For example, an electric motor 32, preferably a micromotor is shown in FIG. 4 with an eccentric mass 44 attached to a shaft of the motor, is used as an electrically drivable vibrating element 32. The electrical vibrating element 32 makes available a vibrating, oscillating, swiveling or other form of mechanical movement. The micromotor used in the particularly preferred embodiment, provides rotation frequencies between 6000 rpm, preferably 8000 rpm, and 12,000 rpm. The outer diameter of the motor housing, including the eccentric mass 44, is between 3 mm, preferably 4 mm, and 8 mm, preferably 6 mm. The housing has a total length without motor contacts of between 10 mm, preferably 12 mm, and 20 mm, preferably 16 mm. The current consumption of the micromotor is between 50 mA, preferably 80 mA and 300 mA, preferably 200 mA. The connection resistance is stated to be 3Ω, preferably 5Ω, up to 20Ω and preferably 15Ω. The motor is operated with a voltage of 0.9 V-1.5 V. These key values permit a sufficient vibration performance and a user-acceptable service life of an AAA or AA battery.

As can be seen in FIG. 4, the micromotor is electrically connected by means of two sprung motor contacts 46 electrically with contacts, which are preferably gold plated, provided on the circuit board 36. The sprung motor contacts 46 ensure that electricity is supplied even when the treatment head 12 with the micromotor therein is deflected elastically. For installation reasons, the motor contacts 46 preferably are not permanently connected with the circuit board 36 but instead, rest on the contacts of the circuit board only under the spring force of the motor contacts. Alternatively to the sprung motor contacts 46, flexible electric leads (such as stranded wires) may be provided fixed to the circuit board 36 and the vibrating element 32. These two solutions enable the micromotor to be arranged at an angle to the circuit board 36. In this case, the circuit board 36 and the micromotor need not be aligned. This permits a high degree of freedom in the design and a better ergonomy for the device.

The micromotor may also be placed closer to the free end region of the treatment head 12 than to the handle 14. This has the advantage that the vibrations are transferred largely over the treatment head 12 with the cartridge-holding mechanism 16 thereof to the razor cartridge and then to the user's skin surface and do not tend to be absorbed through the handle 14 by the hand of the user. At the same time, the soft material, molded into the recesses of the flexible zone 18, absorb vibrations for the handle 14. Likewise, this vibration-damping property is promoted by the neck-shaped tapered outer contour of the flexible zone 18 in the transition region between the treatment head 12 and the handle 14. For the installation, the micromotor preferably is inserted from the treatment head 12 and subsequently connected tightly and permanently with a lid 48 by means of (ultrasonic) welding, gluing, mechanical anchoring etc. and optionally over-molded with soft material.

In an alternative embodiment, it is also possible to connect the electric micromotor, acting as an electric vibrating element 32, permanently, for example, by soldering, with the circuit board 36. In this case, it is mounted on the circuit board 36 as an SMD (surface-mounted device). This embodiment has the advantage that a reliable electrical contact is ensured between the micromotor and the circuit board 36 and the electrical functional unit 30 can be mounted as a whole, including the micromotor. In this embodiment the axis of the micromotor extends parallel to the surface of the circuit board 36.

Aside from producing vibrations or oscillating or swiveling mechanical motions, the micromotor can also find use for other functions. For this purpose, the micromotor can also be used by means of a microprocessor, arranged on the circuit board 36, and a pulse width modulation unit (PWM), connected ahead on the supplying side, as an acoustic or haptic signal generator, in order to transmit information to the user of the wet razor 10 and/or to confirm user interactions. Such secondary tasks preferably are carried out only for a short time of up to 5 seconds and preferably of up to 2 seconds. Secondary tasks are explained by means of examples listed in the following. The pulse width modulation unit may be constructed as a hardware part of the microprocessor or generated with the program of the microprocessor.

By way of example, the micromotor is triggered by means of the pulse width modulation unit in very short intervals, in which the micromotor cannot reach the intended rotational operating frequency. This is brought about in that the pulse width modulation unit passes short supply pulses, which do not permit the rotor to be rotated completely, to the micromotor. At the same time, the rotor is driven only very briefly and pulled back by its internal magnets into almost the original rotation position. In this way, a sort of intermittent movement can be used for producing an audio signal, that is, a noise, a tone or squeak. The micromotor is used in the sense of a synthesizer for producing tone frequencies between 200 Hz, preferably 500 Hz and 1000 Hz, preferably 2000 Hz with a pulse duration of not more than 70% and preferably of not more than 50%. Thereby produced acoustic or haptic signals, as such or in addition to a visual display over the display unit 38, can displayed information, for example, about the change in operating states, as confirmation of a user interaction, if the force is too high or the deflection of the operating head 17 too great, the charge condition of the energy storage system 34, if it is necessary to replace or recharge the energy storage system 34, if the maximum possible use of an exchangeable razor cartridge has been reached, when depressing a reset button, for timer functions, for speed variations, etc.. Since the rotor of the micromotor does not carry out complete revolutions, the signal output described can be used only alternatively to the intended task of the micromotor.

In analogy to the above, a brief change in the frequency by means of the pulse width modulation unit during the intended task of the micromotor, namely the generation of vibrations of the treatment head 12 by complete revolutions of its rotor, can be used for the already previously mentioned confirmation of user interactions. Such a signaling can also be utilized for confirming an exchange of energy storage systems 34, for confirming a key depression, for example for switching on or off, a change in the speed mode, a depression of a reset key when changing razor cartridges, for timer functions, for putting out intermediate times, etc..

In all of the examples listed above, combinations of haptic and acoustic signals can, of course, be displayed. Since preferably a single micromotor is used, these combinations are displayed or produced serially or sequentially. Alternately a loudspeaker or similar sound transmitting device may be used.

Acoustic signals may be instructions on how to use the body care device, confirmation of any user-input settings from actuation of a switching element, progress of a (measurement) parameter such as pressure, battery level, shave counter etc. or signals which are entertaining to the user such as music.

The electric vibrating element 32 in the form of an electric micromotor may represent alternative embodiments of the main loads, that is, for example, a heat-generating electric component, for example, in the form of a resistance, a cold-generating electric component, for example, in the form of a Peltier element, a light-producing components, for example, in the form of a light emitting diodes LED or an electric component generating each acoustic signals, for example, in the form of a speaker. Such main loads can be used individually or in combination of several main loads, as well as in the sense of one or more secondary loads.

The electric functional unit 30 and the individual elements thereof are described in detail in the following by means of FIGS. 6 to 13. Reference is made here to the previous paragraphs with regard to the micromotor used as the main load. As described in the various variations of the embodiments, the micromotor can be a component which is or is not connected mechanically with the circuit board 36. Consequently, the micromotor may or may not be a part of the electrical functional unit 30. The electrical functional unit 30, in the sense of a holding function, has a first holding element 50, which is made from a hard material, for holding the circuit board 36, and, firmly connected therewith, a sleeve-shaped, second holding element 52 for taking up the energy storage system 34 in the form of a battery. The first holding element 50 alternatively may consist of several partial elements of a hard plastic material or of a metal. These may be positioned on one or both sides of the circuit board 36.

The circuit board 36, which carries a large number of electrical components, is the centerpiece of the electrical functional unit 30 shown in FIG. 6. The electrical components are linked electrically in a known manner with metal conductor paths of copper, which may be silver plated or gold plated partially. For reasons of space, the circuit board 36 preferably is equipped on both sides with electrical components. The thickness of the material of the circuit board 36 is 0.5 mm to 3 mm and preferably 1.6 mm, in order to ensure a good inherent stability for the functions named in this publication.

The electrical components preferably are mounted as SMD components on the circuit board 36 in an appropriate, preferably automatic SMD method. The electrical components include the already mentioned microprocessor, resistances, diodes, light emitting diodes (LEDs), transistors, voltage doublers, coils, capacitors, etc. which are connected electrically by soldering to the appropriate conductor paths or are soldered. All connecting methods, such as vapor soldering or reflow soldering are used for this purpose, reflow soldering being preferred.

According to the invention, the wet razor 10 is equipped with a deflection sensor 54, which is capable of generating an electrical signal as a function of the elastic deflection of the treatment head 12 with respect to be handle 14. In a preferred embodiment, the deflection sensor 54 consists of a force-sensitive, force-sensitive or elongation-sensitive resistance, (see FIG. 13). The deflection sensor 54, preferably the force-sensitive resistance (FSR) may be integrated as a discrete electrical component or may be an integrated component of the wet razor. For example, the FSR may have a hard or a soft material with appropriate force-sensitive properties. Preferably, this material is injected in a multi-component injection molding process with the other plastic components into the flexible zone 18 or into the surroundings thereof. Alternatively to the FSR 56, strain gauges, piezo-sensitive elements or other force-sensitive, force-sensitive, extension-sensitive or movement-sensitive components may also be used.

Alternatively, the force on the treatment head 12 can also be determined by the level of the micromotor current, the micromotor voltage, voltage peaks when switching the micromotor on and off (back EMF) or over the pulse width modulation unit.

The preferred force-sensitive resistance FSR 56 is fixed by means of adhesion technology, mechanically, a printing technique etc. on a flat side of the circuit board 16.

Alternatively to installing the FSR on the circuit board 36, the force-sensitive resistance FSR 56 can also be used at a different place of the wet razor 10, at which a change in force during use arises. In this case, electric leads are run from the FSR to the circuit board 36. These electrical leads and the FSR 56 can be over-molded partly or completely with a hard or soft material in order to seal them. In this connection, reference is made to WO 2004/030891.

As shown in FIGS. 8 and 9, a force-sensitive or force-sensitive section is disposed on a tongue-like continuation 58 of the circuit board 36 and, in the installed state of the electric functional unit 30, positioned close to the flexible zone 18, in the case of a wet razor 10, preferably on the upper side of the circuit board 36.

The display unit 38, in the form of an LCD display, is fixed positively or non-positively on the upper side or the underside of the circuit board 36, preferably with snap-on noses molded for this purpose at the first holding element 50. These exert a force on the display unit 38. The force acts over an electric contact element, commonly known in the art as a "zebra," on the circuit board 36. A satisfactory contacting of the LCD display with the circuit board 36 is ensured by the force on the "zebra," which is located sandwich-like between the display unit 38 and the circuit board 36 and has a number of electrically conducting contact compartments, which are insulated from one another. In order to increase the force, the first holding element 50 may consist of partial elements of a hard plastic material and/or of metal. Appropriate conducting parts, connected with the pins of the microprocessor, correspond in position and size to the contacts of the display unit 38, provided by the "zebra." Alternatively, the display unit 38 may, of course, also be contacted electrically with the circuit board 36 by means of more flexible conducting parts. The LCD display is separated from the circuit boards 36 by the thickness of the "zebra." For reasons of space, this distance is selected so that other electrical components, listed above, can be disposed on the circuit board 36 under the LCD display next to the "zebra."

Figure 23:
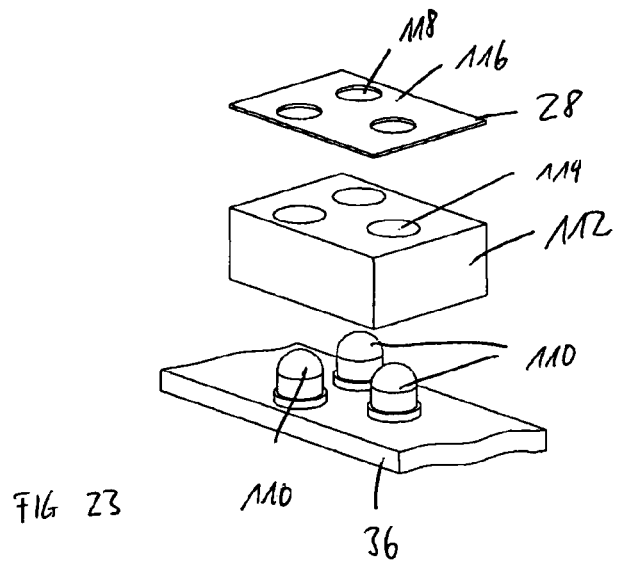
FIG. 23 shows an exploded portion of a display including LEDs.

Alternatively, the display 38 can include one or more LEDs. As previously mentioned, the LEDs are preferably mounted directly on the circuit board 36 as SMDs. In order that light from any one LED is correctly seen in its assigned position and does not spread to other positions, light piping or a light chimney is used between the circuit board 36 and the inner surface of the window 28. In FIG. 23 an exploded portion of a display including LEDs is shown. LEDs 110 are directly mounted to the circuit board 36. Light chimney 112 fits over the LEDs and extends substantially from the circuit board to the inner surface of the window 28. Light chimney 112 is preferably made from an opaque non-conductive material such as a molded thermoplastic. The light chimney 112 includes passages 114 that channel light from any respective LED to the window. The window 28 includes opaque portions 116 and transparent or translucent portions 118 where light from the respective LED can be seen by a user. To minimize power consumption the LED's may be switched off after a certain time period. This time period may alter and not depend on the use of the switches but the start of use determined by the force sensor. Another option to save power is to use one LED to display a summarized status of several display statuses. In particular the summarized status indicates the status of the battery level and the shave counter (number of uses) which will be described at a later stage.

Electrical supply contacts between the energy storage system 34 and the circuit boards 36 for supplying the electrical components are soldered to the circuit board 36. The first holding element 50 may act as an additional positioning aid and serve to fix the supply contacts.

The first holding element 50, which preferably is molded by means of an injection molding technique from a hard material or form partial elements of a hard material and/or metal, preferably from POM, not only holds and fixes the circuit board 36 and the display unit 38, but also fixes and positions the electrical functional unit 30 in the recess 60 of the handle 14, which is provided for this purpose, by a mechanical or other active connection with appropriate edges, stops and guides.

Two key elements 62 are suspended flexibly at the first holding element 50. Preferably, these are produced as integrated components on the first holding element 50 by means of injection molding. In the installed state, the key elements 62, on the one hand, act together with the switching membrane 40, disposed on the upper side and with snap-on discs 64, disposed correspondingly on the circuit board side and form the switching elements 42. The dimensioning of the connecting bridges 68, connecting the key elements 62 with a basic framework 66 of the first holding element 50, enables the restoring force for the key elements 62 to be set and, by these means, ensures a pleasant haptic and a reliable positional restoration during the actuation of the key elements 42.

The first holding element 50 has a force element 70 in its free end region oriented on the vibrating element side. Preferably, this is also produced by means of injection molding as an integrated component of the first holding element 50. The force element 70 is connected over a bridge or a film hinge flexibly with the basic framework 66 of a first holding element 50. Essentially, it is plate-shaped and, with its sensor surface side facing the circuit board, covers a significant portion of the force-sensitive or force-sensitive region of the FSR 56 (compare FIGS. 6 to 8). On the sensor surface side, facing the FSR 56, as well as on the opposite actuation surface side, the force element 70 is equipped with actuating cams 72. The actuating cam 72 on the sensor surface side acts on the force-sensitive or force-sensitive region of the FSR 56 and the actuating cam 72 on the actuating surface side acts together with an actuating extension 74, which is molded from a hard material at the treatment head 12, in such a manner, that the force element 70 is deflected during an elastic deflection of the treatment head 12 with respect to the handle 14 in the direction of the FSR 56. Alternatively, it is, of course, also possible not to form the actuating cams 72, so that the force element 70 interacts directly with the actuating extension 74 and the FSR 56. In this connection, it should be noted that the first holding element 50, at which the force element 70 is formed, may be constructed in one part, as well as in several parts and preferably in two parts. In the latter case, the parts preferably are locked mechanically with one another or connected by means of a film hinge with one another.

In an alternative embodiment of FIG. 4, the actuating extension 74 interacts directly with the FSR 56. However, this variation is less preferred, since the actuating extension 74 exerts asymmetrical forces on the FSR 56 and, in any case, has a minimum movement component in the longitudinal direction at its disposal. This may affect the service life of the FSR 56 and, if the worst comes to the worst, damage the latter. For this reason, the solution by means of the additional force element 70 is preferred, since this equalizes the force of the actuating extension 74 and prevents mechanical abrasion of the FSR 56 resulting from the longitudinal or lateral movement of the actuating extension 74.

In the following, the electrical components of the inventive wet razor 10, preferably electrical components, which form a so-called user interface with the information exchange, will be dealt with in detail. In this connection, it is assumed that the information from the wet razor 10 can be displayed individually or in combination that is, with a certain redundancy. Moreover, it is possible that signals or information in different form can be transmitted to the user depending on the use or environment. In general, it is a fact that the electrical components, predetermined for the exchange of information, can each be controlled by the microprocessor or the microcontroller.

The following types of information can be displayed:
visual information by the LCD display, which functions as a display unit 38 and in which individual segments can be switched on and off. When a certain value is reached, the individual segments can blink with a varying blink interval. In particular, the segments can form digit segments for representing numbers. Further visual information can be displayed over LEDs with different colors and in different positions. In particular, when a specified value is reached, an LED can be switched on or off, change color or blink with varying blink intervals. The intensity of the light of the LED can be controlled over the pulse width modulation unit with different resistance values coupled to the individual LEDs. In particular, it is proposed that different light intensities of, preferably, similarly colored LEDs be displayed in order to indicate a visual degree of measurement for the progress or intensity of a (measurement) parameter.

acoustic signals as well as haptic signals or information can be generated by the micromotor or a loudspeaker over the pulse width modulation unit. In the case of acoustic or haptic signals, the progress of a (measurement) parameter can also be displayed to the user by means of the intensity (audio frequency, vibrational frequency) or a change in the intensity.

All of the electrical communication elements mentioned, individually or in combination, can acknowledge user actions, confirm the attainment of specified limiting or target values, indicate the status of the energy supply system 34, signal the pending exchange of the razor cartridge, indicate an excessive force on the treatment head 12, state the attainment of a neutralization number or point to an active operation state on the basis of a deflection of the treatment head 12. Measurement parameters, such as the intensity of the force on the treatment head 12, the micromotor speed, the degree to which the energy storage system is charged, the number of uses of the treatment attachment (e.g. the razor cartridge in the case of the wet razor), etc. are available for the information output described above with an intensity adapted to the (measurement) magnitude or a dependent intensity.

The LCD display for the visual signaling may be mounted above either side of the circuit board 36. The thickness of the lens of the LCD display is 1 mm to 3 mm and preferably 2 mm. The distance of the outer surface of the LCD display from the inner surface of the window 28 preferably is 0.5 mm, particularly 1 mm to 4 mm and preferably 2 mm. The LCD display passes on information, generated by the microprocessor, to the user.

In the particularly preferred embodiment, the LCD display has two digits, which can be represented fully, for representing a numerical range from 0 to 99 for a use counter, which counts the number of uses of the treatment attachment or measures the use time. Alternatively, it is also possible to use 1.5 digits for representing a numerical range from 0 to 19. If a specified or calculated value of the uses, that is, the uses of a razor cartridge, is reached, the digits blink in order to indicate to the user to replace the razor cartridge or the treatment attachment.

Beyond that, the LCD display can represent speed steps of the electrical vibrating element 32. In this connection, several discrete steps (e.g. slow, medium, fast) are coupled to predetermined speeds of the micromotor. Preferably, the information is displayed in parentheses or by other, preferably non-numeric symbols, e.g. the number of pairs of parentheses corresponding to a specified speed step.

Additionally or alternatively, the display unit 38 has the possibility of representing 1 or more preprogrammed, selectable micromotor speed profiles, which have a sinusoidal, a pulsating, a saw tooth-shaped, a triangular or a pulse-shaped profile or a combination thereof. In this connection, the speed of the micromotor of the electric vibrating element 32 changes during the use of the wet razor 10 according to a repeating frequency pattern, which is pre-programmed in the microprocessor. Furthermore, the LCD display, additionally or alternatively offers the possibility of representing a selected automatic step. For this automatic step, the speed of the micromotor of the vibrational element 32 is automatically adjusted depending on the signal from the deflection sensor 54, preferably in the form of an FSR 56. In particular, corresponding to the force, the speed of the micromotor of the electric vibrational element 32 is changed, preferably increased, preferably at a higher force on the treatment head. The change can takes place essentially linearly. However, if the force is excessive, the speed of the micromotor is limited at a certain specified minimum or maximum value. Alternatively to the fixed minimum or maximum values, it is possible to adapt the adjustable micromotor speed range to each individual user. With that, each individual user, independently of the maximum forces on the treatment head 12 achieved in the use, can profit from the full band width of available micromotor speeds. For this purpose, the maximum force values, which are determined by means of the deflection sensor 54, can be determined over a sliding average value in the memory of the microprocessor.

Accordingly, the micromotor speed range can be set between a fixed or also a sliding minimum lower value and the sliding maximum average value of the individual user. With that, there is a smaller or a larger speed change within a defined force change, depending on the user.

Moreover, the LCD display can also display the force acting on the treatment head 12. For this purpose, for example, blocks of different size or rectangular representations can be used. The number of blocks arises once again from a measured value for the deflection, for example, from the resistance or voltage measured by the FSR 56 of the deflection sensor 54. Alternatively, the previously given alternative measured values, determined, for example, over the micromotor, can once again also be used here.

As already mentioned, the LCD display can also display the charging state of the energy storage system 34. For example, in a simple embodiment, a display can be activated in the event that a battery voltage falls below a specified value between 0.1V and 1.1V and preferably below 0.9V. Alternatively, the display of the charging condition may have 2 to 6 and preferably 4 steps. These steps also correspond in each case to a specified voltage of the energy supply system 34. If the voltage falls below a specified value in the case of this embodiment, the display of the charging condition is extinguished in order to alert the user that the capacity of the energy storage system 34 is exhausted. The microprocessor, already mentioned previously, has a reference voltage, which can be used for the purpose of a comparison with the voltage of the energy storage system 34. If a rechargeable battery is used as energy storage system 34, the anticipated charging time can be calculated from the remaining voltage of the battery. This can be done continuously, so that the still remaining charging time can be calculated and displayed during the charging process.

As an alternative to the LCD display, it is also possible to use LEDs or OLEDs. They serve the same purpose, namely to display information generated by the microprocessor to the user. Preferably, the colors green, red and yellow are used. Alternatively, it is, of course, also possible to use the LEDs together with the LCD display in the sense of a redundant information output. This is advantageous particularly when the LCD display is not visible or not visible optimally, for example, because it is covered by the hand of the user. In this connection, a single LED may assume different signal states, for example, be switched on or off, blink or exhibit different light intensities or colors. These different operating states can be used as an indicator, particularly for the use counter, a speed display, a force display or the display indicating the degree of the charge of the energy storage system 34 as well as for signaling by a timer (specified use duration for a correct use) or for the output of intermediate times during a use.

The already mentioned microprocessor is specified for processing signals of a sensor or of a load, preferably of the deflection sensor 54, of measurement results, of calculations and/or inputs of the user and, in accordance with a specified program, supplies output signals for the triggering of the electric components, such as the LCD display, the LEDs, the micromotor, of resistances, of a Peltier element, a loudspeaker etc. The microprocessor is preferably configured for a supply voltage of 0.9 to 1.5 V and, for reasons of space, can be supplied directly from a 1.5 V voltage source, such as an AA or AAA battery. Alternatively, it is possible to use a voltage converter, which adapts the output voltage of the energy supply system 34 to the required supply voltage of the microprocessor. In this case, microprocessors with a higher operating voltage of up to 5 V and preferably of 3 V can be used Preferably the body care device holds only one single microprocessor for controlling the display functions/ output signals, the loads e.g. the motor, loudspeaker etc. and processing the signals of the sensor (in case of need also storing).

The microprocessor, used in the preferred embodiment, has a volatile memory RAM of 64 bytes to 1024 bytes and preferably of 128 bytes for the data and a ROM or flash memory of 256 bytes up to 64 kbytes and preferably of 2 kbytes for programs. Furthermore, the microprocessor is equipped with a non-volatile memory EEPROM with a capacity of 16 bytes, which makes it possible to store a calibration table for the deflection sensor 54, after the latter has been installed. However, other calibration values, such as the micromotor speed, can also be stored. In addition, the microprocessor preferably has at least one A/D (analog-digital) converter, which makes it possible to convert analog measurement data, for example, data from the deflection sensor 54 or the micromotor, into digital data. The pulse width modulation unit for triggering the electric vibrating element, that is, the main load, as well as further subsidiary loads, already listed above, is also integrated in the microprocessor. The pulse width modulation unit is preferably present as hardware and not part of a program. As already mentioned, the microprocessor also generates voltage comparison values. It can be put in a sleep mode, in which the microprocessor itself uses less than 50 µA, preferably less than 20 µA and most preferably less than 10 µA. The microprocessor has more than 6 inputs or outputs, preferably 8 to 28. Moreover, it is equipped with a timer function, which can be used, for example, for measuring time for the duration of use and/or for determining interim times.

If additional computational or memory capacity is required, e.g. to monitor brushing behavior if the body care device is a toothbrush, the device can be provided with means to communicate with an external processor such as a Personal Computer or smart phone. Communication means can include 'wired' technologies (wire-based technologies) such as a RS232 or USB port 100 on the razor, preferably a mini-USB port. Alternatively the razor's circuit board 36 can be provided with wireless communication technologies such as WLAN or Bluetooth capabilities. As the body care device that is e.g. a razor or toothbrush is typically used in a wet environment a RS232, USB or mini-USB port can be provided with a removable water-proof seal or cover. This port covering element can either be formed of a hard, a soft or a combination of hard and soft plastics.

Figure 24:
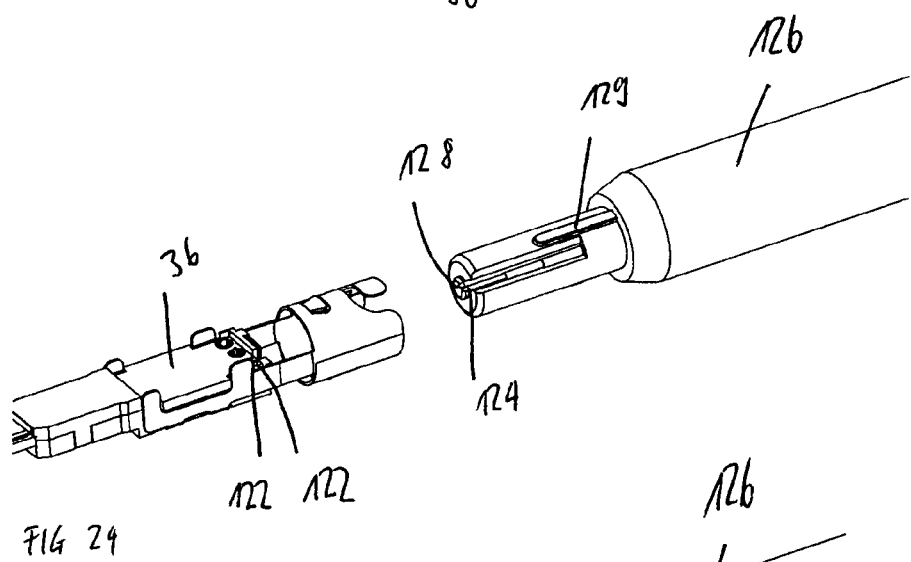
FIG. 24 shows a data read-out interface non-connected.
Figure 25:
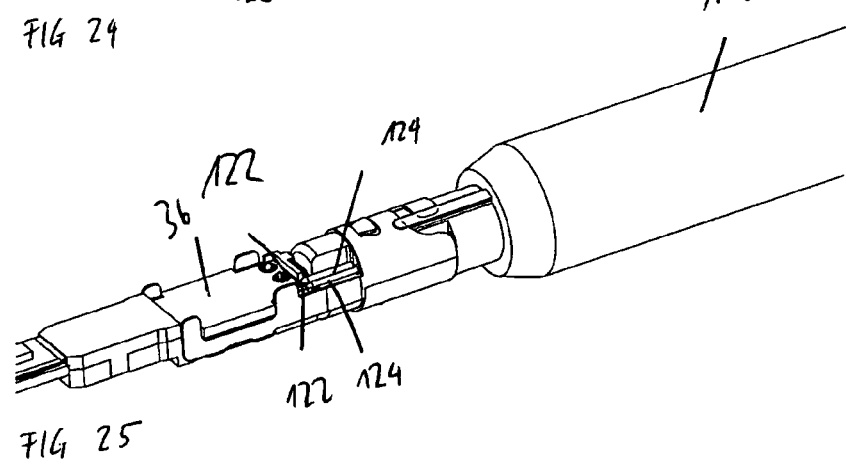
FIG. 25 Shows the read-out interface of FIG. 24 connected.

In one embodiment the circuit board 36 is provided preferably at the rear end with contact pads 122 which may be accessed through the battery compartment with contact pins 124 establishing contact to the external processor. In this embodiment an end cap 20 is providing the required waterproof seal. This interface is shown in FIGS. 24 and 25. The read-out element 126 is connected to an external processor for example a Personal Computer. As shown the read-out element 126 can be inserted into the battery compartment. By inserting the electric circuit to supply the circuit board and the other elements with power is closed by the pin-contact element 128 and the stripe-contact element 129. The two elements build the same circuit as a battery. The pin-contact element 128 contacts the same place as the plus pole of the battery and the stripe-contact element 129 contacts the second holding element 52 to close the electric circuit. By inserting the read-out element 126 a data connection between the contact pads 122 and the contact pins 124 is established Preferably the body care device holds only one single microprocessor for controlling the display functions, the loads e.g. the motor, loudspeaker etc. and the communication means to the external processor.

The communication between the body care device and the circuit board 36 by means of above mentioned communication technologies such as USB, WLAN or Bluetooth will allow the user to monitor the individual parameters of use stored in the memory of the microprocessor. Based on these parameters the user may wish to adjust certain output functions of the program of the body care device e.g. display means, motor speed or timer functions. In this sense the above mentioned communication technologies will allow bi-directional transfer of information between the body care device and the external processor such as PC or smart phone. More over these technologies allow real time monitoring of parameters during the use of the body care device. For real time monitoring of parameters the wireless technologies such as WLAN or Bluetooth are preferred. In particular the applied force will be monitored in case of a toothbrush to avoid excessive brushing force. In addition it will be desirable to store every individual use and the respective parameters. Naturally the memory of the body care device will not be sufficient in size. Therefore it is desirable that the body care device establishes at every use or occasionally a connection to the external processor to pass on the collected data for further analysis of a dedicated external software. Naturally this will be possible preferably with a wireleses communication technology such as WLAN or Bluetooth. In case of a toothbrush the summarized data may be discussed with the user's dentist during the yearly check. Again based on the dentist's feedback the user may wish to adjust certain output functions of the program of the body care device to adjust the performance of the body care device to the individual habits to optimize the over all performance.

The voltage converter, which is optionally present, converts the voltage of the energy supply system 34 to the operating voltage of the microprocessor. Above all, it is used when a microprocessor with an operating voltage of 1.8 V to 3 V and/or LEDs are used with an energy supply system 34 having an output voltage about 1.5v (e.g. a AA or AAA battery). The current consumption of the microprocessor during the sleep mode is preferably less than 50 μA as mentioned above. Moreover, transistors, used in amplifying circuits, permit the micromotor to be operated also with higher currents, which cannot be made available directly by the microprocessor. At the same time, the microprocessor then triggers the transistors over the pulse width modulation unit. Because of the lower power loss and the minimal driving power, field effect transistors are preferred over bipolar transistors.

The FSR 56 of the force-sensitive, pressure-sensitive or strain-sensitive deflection sensor 54, shown in FIG. 13, has, depending on the respective load, an electric resistance between 3 kΩ at a maximum load and typically up to 2 MΩ in the load-free state, and also resistances up to more than 2 mΩ in the load-free case. The FSR 56 is an electrical component, which is known to those of ordinary skill in the art, having several sheets printed with an electrically conducting ink which are stacked upon one another and change their resistance under force. Another type of FSR comprises a body of force-transducing-rubber (FTR) that also changes resistance when force or pressure is applied. It is also possible that the FSR 56 is integrated directly by the application of the force-sensitive ink on an appropriate network of (etched) conducting parts present on the circuit board 36. The FSR 56 is connected directly with the microprocessor, so that an additional amplifier for the output signals of the FSR 56 can be omitted. The microprocessor measures and processes voltage changes over the FSR 56 by means of an A/D converter integrated into the microprocessor.

The voltage changes, measured over the FSR 56, can be used for evaluating for the following tasks:

For an automatic start function, the FSR 56 can be placed at an interrupt input, which is active in the sleep mode. In this connection, the FSR 56 has only a digital function— if the voltage change is sufficiently large, the processor is shifted into the wake mode. This is the preferred case. Alternatively, one or more voltage measurements could be made within a specified time, such as five measurements within 1 seconds to 4 seconds (so-called polling). If a threshold value is exceeded, the microprocessor is shifted into the wake mode. This solution requires more energy overall. In the wake mode of the processor, the voltage change is evaluated quantitatively over the integrated A/D converter and, at the same time, the actual force on the FSR 56 is determined.

For an automatic start function, the microprocessor is reset from the wake mode into the sleep mode if no voltage change is detected over the FSR 56 within a certain time, for example, a time shorter than 2 minutes and preferably of about 30 seconds. As a result, the micromotor and all other subsidiary loads are switched off. Only the voltage converter, which may be present, and the microprocessor remain for a regular "interrupt polling" of the FSR 56 or an additional movement sensor 76 in a sleep mode. The additional movement sensor 76 is shown, by way of example, in FIG. 12 is preferably fastened mechanically to the circuit board 36 and contacted therewith electrically. It has essentially four bar contacts 78 disposed in lattice fashion with a metallic ball 80, which is free to move therebetween and can complete a circuit between adjacent bar contacts.

For a use counter function, the use counter is indexed (increased or decreased) by one unit for the number of uses, wherein one or more voltage changes have been measured over the FSR 56 within a certain time, for example, 10 to 50 voltage changes within 1 minute to 5 minutes.

For a force-measuring function, appropriate load results are displayed optically, acoustically and/or have haptically over the FSR 56, as a function of the voltage, to the user over the display unit 38, the electrical vibrating element 32, etc. Depending on the load or of the force, this information output can be passed on to the user continuously or when a specified force is reached, for example, the value of a force alarm, over the signaling transmitters described.

For automatic adjustment of the micromotor speed the micromotor speed is controlled as a function of the voltage over the FSR 56. The speed of the micromotor can be adjusted proportionally, inversely proportionally, hyper-proportionally, inversely hyper-proportionally, hyper-proportionally or inversely hyperproportionally. Of course, the voltage over the FSR 56 can also be used for adjusting other main or subsidiary loads.

With respect to the FSR 56, it should be mentioned that the latter can be operated with a certain prestress, that is, a force over the actuating cam 72 of the force element 70, that is present even in a shaving load-free case. This prestress preferably is 0 or very small, that is, less than 1 N and preferably less than 0.3 N. A small force leads to an increase in the service life of the FSR 56 and makes minimal power consumption possible in the sleep mode.

With that, it is ensured that there is a maximum change in the resistance over the FSR 56 when the treatment head 12 is deflected flexibly. The resistance change of the FSR 56 over its working force range can include approximately linear and non-linear regions. Typically the response curve of FSR 56 is of the form $$y=a/x^b+c$$

where: y=resistance (in kΩ)
x=applied force (N)
a, b, c are constants

Preferably, the analysis of the change in resistance of the FSR 56 is employed in the (approximately) linear range. However, in order to include the largest possible change in resistance, nonlinear regions of the change in resistance can also be analyzed. These can then be converted by means of correction factors based on empirical values by the software in the microprocessor, in order to produce a linear relationship between the force on the treatment head 12 and the FSR 56 signal. For this purpose, preferably Tables are stored in the memory of the microprocessor (i.e. a look-up Table). In order to analyze the change in resistance of the FSR 56, the voltage change over the FSR 56 is measured and evaluated.

Since a measurement of load or force, a force alarm or the automatic step for adjusting the speed of the micromotor depend on the contacting force of the treatment head 12 and, with that, on the deflection of the treatment head 12, the FSR 54 preferably is calibrated after being installed and a corresponding calibration Table is stored on the EEPROM of the microprocessor. In this way, installation tolerances, voltage deviations of the energy supply system 34 and component tolerances are compensated for and the force alarm value can essentially be fixed at a constant value for a relatively large number of individual wet razors 10.

In a further embodiment, a snap-on disk, which only sends an on and off signal to the microprocessor, may be used instead of the FSR 56. The mechanical implementation and control of further processes is converted in a manner analogous to that employed with the FSR 56. This solution can be produced particularly cost-efficiently. However, it has the disadvantage that information concerning the magnitude of the load cannot be obtained continuously and only a binary signal is available. Of course, conclusions concerning the force on the treatment head 12 can be derived from the length (time period) of the signal.

As already mentioned above, a movement sensor 76 may additionally be integrated on the circuit board 36, as shown, for example, in FIG. 11. The movement sensor 76 is shown in detail in FIG. 12. The metallic bar contacts 78 as well as the metallic ball 80 preferably are gold-plated. During a movement of the wet razor 10, the metallic ball 80 contacts different adjacent bar contacts 78 and, in so doing, enables a binary movement signal to be transmitted to the microprocessor. Alternatively to the metallic bar contacts 78 arranged in lattice fashion, it is also possible to use a cage of nonconducting material above a circuit board 36, which is provided with appropriate conducting parts.

The following functions of the FSR 56 can be supported by installing the movement sensor 76 alternatively or additionally:

For the autostart function, one and/or more movement measurements may be detected within a certain time, for example, five changes within 1 second to 4 seconds, in order to switch the microprocessor from the sleep mode to the wake mode. Additionally, the micromotor functioning as an electric vibrating element 32, can also be changed over into an active operating state.

For the autostart function, the microprocessor can be switched from a wake mode to the sleep mode and the micromotor switched off in the event that there has not been a change in the movement within a certain time, for example, a time of less than 2 minutes and preferably of less than 30 seconds.

For the function counting the number of uses, the use counter can be incremented by 1 unit if there have been one or more changes in the movement signal in a certain period of time, for example, 10 to 50 changes within 1 minute to 5 minutes.

The above mentioned, optionally usable further snap-on disks for producing a binary load signal consists of stamped metal sheets, which preferably are gold plated at least partly in their contact zones. The further snap-on disks in this case are connected mechanically with the circuit board 36. This applies analogously also for the snap-on disks 64, which interact with the key elements 62. During an actuation of the switching membrane 40 or a corresponding deflection of the force element 70, the snap-on disks 64 or the further snap-on disk are deflected in a zone, provided for this purpose, as far as the circuit boards 36 and initiate a corresponding electric contact. As the load disappears, the snap-on disks 64 or the further snap-on disk, because of the spring action of their material, snap back into the original position, in which they do not make contact. As a rule, only brief signal pulses are produced by the snap-on disks 64 or the further snap-on disk. Several functions can be coded by the duration of the load and, with that, by the duration of the signal produced by the snap-on disks, such as a function 1 during a short actuation of less than 1 second and a function 2 during a long the actuation of more than 2 to 3 seconds. The output signal of the snap-on disks 64 or of the further snap-on disk is passed on directly to the microprocessor, by which it is processed. The same effect can be used for qualifying the contacting force of the snap-on disk used instead of the FSR 56.

The electrical power-supplying contacts of the energy storage system 34 preferably are constructed as stamped metal parts, which are connected electrically with the circuit board 36 and optionally fixed in position mechanically by the first holding element 50. The supplying contacts surround the energy storage system 34 at least partly and exert a spring force on the latter in a known manner. The supply contact, at which there is a positive voltage, is shaped as a short, one piece, stamped metal part, whereas the supply contact for the opposite negative pole is formed can be two pieces.

Figure 21:
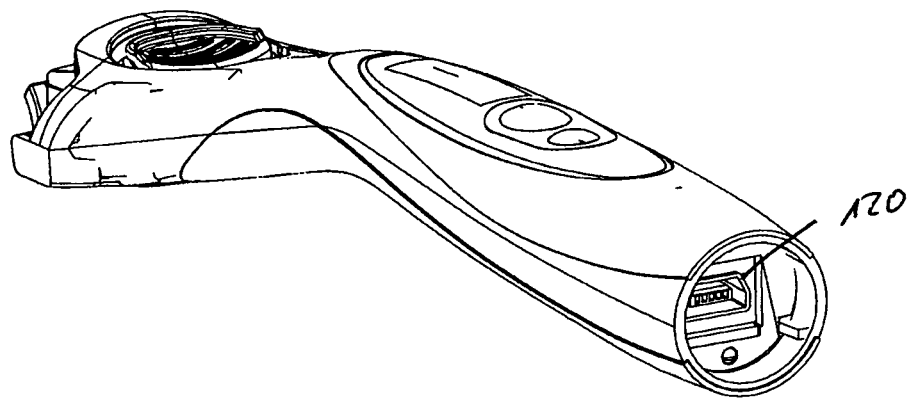
FIG. 21 shows an example of the application of the invention in a razor with an USB interface.
Figure 22:
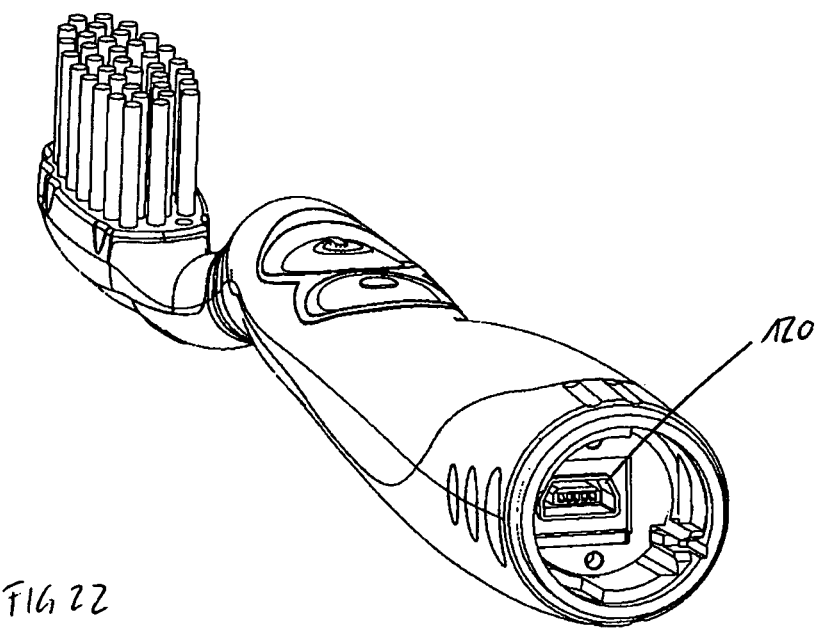
FIG. 22 shows an example of the application of the invention in a toothbrush with an USB interface.

As already mentioned, a front part of the negative supply contact is connected electrically with the circuit board 36. A rear part of the negative supply contact is integrated in the end cap 20. When placing it on the free end region of the handle 14, the end cap 20 is connected over a bayonet connection mechanically with the handle 14 and electrically with the front part of the negative supply contact. In one embodiment the supply contact of the end cap 20 may also electrically communicate with a 'wired' communication port described previously. In particular a USB port may be directly mounted on the circuit board and the supply contact of the end cap 20 may electrically contact to the metallic 'frame' of the USB port. In FIGS. 21 and 22 a possible arrangement of the USB/mini-USB port at the rear end is shown for a razor and a toothbrush. The needed protection cover is not shown in these figures. In this embodiment the appliance is realized with a integrated rechargeable battery. The port can be used as power transfer and also data transfer interface. The end cap 20 and connections can be formed similar as disclosed in WO 2005/

046'508 A1 which is hereby incorporated for reference. In the described embodiment the cap respective the integrated metal piece closes the electric circuit by touching the outer frame 120 of the USB/mini-USB port and the contact bridges or other contact elements. But it is also possible to design the USB/mini-USB port just for one of the features either power transfer or data transfer. So it can be used for rechargeable or non-rechargeable appliances. The USB or mini-USB port can also be arranged in other positions on the handle. For example more in front and standing more or less perpendicular the outer shape of the razor. In this case the preferred cover is made from a soft-material. In circuit board near regions of the handle it is possible to mount the USB directly on it.

A seal of a soft material is molded or a conventional O ring is disposed at the free and region of the handle 14 in order to seal the cavity, formed in the electrical functional unit 30 for accommodating the energy storage system 34, tightly.

As already mentioned, the energy storage system 34 preferably is one or more batteries that can be disposable or rechargeable. Preferably, a disposable AAA battery with a capacity of 750 mA/h and preferably of 1,200 mA/h is used. Alternatively, AA batteries or other batteries e.g. button batteries can also be used. In the case of rechargeable batteries, preferably NiMH types are used. When equipped with a rechargeable battery, the inventive wet razor 10 can be charged by known procedures by means of induction or over a transformer with an appropriate cable connection. It is also possible to use more than one battery in the inventive wet razor 10, provided that there is sufficient space. In this case, it is possible to do without the already mentioned voltage converter since operating voltages of about 3 V can be made available in this way, e.g. by connecting batteries in series.

In order to maximize battery life, the entire electrical functional unit 30 should require a current of less than 100 µA and preferably of less than 70 µA in the sleep mode. In particular, when the inventive wet razor is used as intended with a vibration micromotor, the current flowing should be less than 150 mA and preferably less than 100 mA in the wake mode. The same applies for the case in which the treatment head 12 described is equipped with brushes for a mascara brush and not with exchangeable razor cartridges as in the case of a wet razor 10. If the treatment head 12 is equipped with an appropriate brush arrangement for a toothbrush and with a vibrational micromotor, the current flow should be less than 300 mA and preferably less than 200 mA. However, if the whole of the previously described arrangement is used for a toothbrush with a swiveling or a rotating brush head, current flows of less than 800 mA and preferably of less than 600 mA arise.

The functions, implemented in the inventive wet razor 10, are summarized once again here. The main function of the inventive electric wet razor 10 is to provide a wet shave, enhanced by vibration provided by the electric vibrational element 32, for improved hair cutting and reduced skin irritation. The electrical vibrational element 32 as well as the microprocessor can be switched on or off by pressing the switching elements 42 in the sense of a main switch or can be switched on or off automatically as previously described and as follows.

The microprocessor is shifted from its sleep mode to the wake mode by implementing the autostart function, that is, by switching it on without actuating the switching elements 42. The user is made aware of this (individual or combined signals) by the display unit 38, the electric vibrating element 32, etc., by way of an appropriate optical, acoustic or haptic signal. Preferably, for this change in mode, the electric vibrating element 32 is not switched on directly, but only when the user actuates a switching elements 42. Several possibilities are available for initiating the autostart function.

For example, by means of a sensor, preferably the deflection sensor 54 or the movement sensor 76, the microprocessor can determine over a certain period of time whether the wet razor 10 is in use as intended or, alternatively, if there is contact of the wet razor 10 at a surface. For the latter variation, the wet razor 10 has, at or barely below the surface, two surface zones of electrically conductive material, such as an electrically conducting plastic, preferably an electrically conducting hard material, which combines with the hard material of the basic body during the injection molding (fuse joining during multicomponent injection molding), an electrically conducting paint or metallic or metallized surfaces. When not under load, the surface zones do not touch one another. The electrically conducting surface zones are connected electrically with the circuit board 36 and, furthermore, with the microprocessor. Upon contact of at least two surface zones, an electric circuit is closed by way of the user. At the same time, an electric current change, a resistance change, a voltage change or a capacitance change is used as measurement parameter. This can be noted by the microprocessor even when at least two surface zones are immersed in water and the autostart function is activated correspondingly.

The autostop function switches off the electric vibrating element 32 after a specified time and shifts the microprocessor into its sleep mode. This function can be initiated either by taking the output signal of sensors, such as the deflection sensor 54 or the movement sensor 76, into consideration, while disregarding sensor signals, in the absence of contact between the electrically conducting surface zones or also when the supply voltage of the energy storage system 34 falls below a specified values, which causes the vibrational element 32 to be switched off.

The number of uses of an exchangeable razor cartridge is determined by the use counter function in order to provide the user with appropriate information for changing a razor cartridge when a specified or calculated number of uses has been reached. At the same time, the counter number is indexed by 1 for each use or the measured use time is added up. The sensor signals as well as their variation over time, the use of the electric vibrational element 32 and the use of the switching elements 42 with their variation over time or a combination of the qualifiers named is called upon to determine when the wet razor 10 is in use. For example, an appropriate signal for exchanging a razor cartridge is generated when a fixed value, stored in a program, for the number of uses is reached. An output of the electric vibrational unit 32 then takes place as discussed, for example, by blinking digits on the LCD display or by switching on or blinking LEDs or by an acoustic or haptic signal. Alternatively, a calculated value can also be used for initiating an instruction to exchange the razor cartridge. This calculated value then is preferably a rolling average of the previous number of uses per razor cartridge, which depends on the behavior of the user.

The use counter can be reset by the user, for example, after a razor cartridge is exchanged. The resetting is initiated, for example, by a short actuation of a switching element 42 or a combination of switching elements 42. Alternatively, the use counter may also be reset automatically, when the microprocessor has recognized the exchange of razor cartridges independently. Preferably, the microprocessor recognizes a difference between an old and a new razor cartridge that is, it can differentiate razor cartridges from one another. This differentiation may be made by means of an inductive contact between a razor cartridge and a wet razor 10, by mechanically initiating a switch during the exchange of razor cartridges, by RFID communication between the razor cartridges and the wet razor 10 or by means of a reading head for magnetic strips or for an EAN (European article number) on the razor cartridge.

The signal of the deflection sensor 54, evaluated by the microprocessor, is used for the function for determining and putting out the contacting force of the treatment head 12 at the skin surface. The contacting force determined can be displayed as a continuous measurement result or when a specified maximum value is exceeded, or alternatively, for example, by blinking symbols in the LCD display, by switching on a blinking or color change of an LED and/or an acoustic or haptic signal indicated by the electric vibrational element 32 or a loudspeaker.

Alternatively, aside from a signal of a force-sensitive, force-sensitive or expansion-sensitive sensor, other measurement parameters of the main or subsidiary loads, such as the micromotor current, the micromotor voltage or voltage peaks when switching on or off of the micromotor, functioning as electric vibrational element 32, can also be used.

Because of the contacting force that has been determined, the operating state of the electric vibrational element 32, forming the main load, preferably the speed of the micromotor, can be adjusted appropriately. As already mentioned above, such adaptations of the speed of the micromotor may be proportional, inversely proportional, hyperproportional, inversely hyperproportional or hypoproportional or inversely hyperproportional. Preferably, when the contacting force is higher, the micromotor output speed of the wet razor 10 is increased correspondingly. When the inventive arrangement is used in the sense of a toothbrush that is, when the treatment head 12 is equipped with an appropriate arrangement of bristles, the micromotor output speed can be advantageously reduced at higher contacting forces.

For determining the values of the contacting force, basically the values measured during a use as intended are compared with those of the stress-free basic state. The recording of measured values in the stress-free basic state permits a calibration of the contacting force measuring device and serves for compensating for individual tolerances of the sensors, of the energy storage system 34, etc..

The operating state of the micromotor output speed or of the strengths of vibration of the electric vibrational element 32 can be adjusted automatically as previously discussed. Alternatively, an operating state can also be adjusted by a user manually actuating switching elements 42 with an appropriate actuating time. Moreover, a selection of discrete vibration steps, which are pre-programmed, preferably in three steps, such as slow, medium of fast, is possible.

In addition, pre-programmed vibration profiles can also be initiated by way of an appropriate program selection. Likewise, it is also possible that the speed of the micromotor or the strength of the vibration can be adjusted as a function of the actuation time of the switching elements 42. The step, set when the switching element 42 is released then remains selected. Instead of being adjusted in discrete steps, the micromotor speed can also be adjusted steplessly. In this case, the speed steps, indicated on the display, correspond to the nearest discrete step. Alternatively, a wheel, like that shown in FIGS. 18 and 19 for mascara brushes, can also be mounted at the device, in order to adjust the strength of the vibrational (energy supplied to a main or subsidiary load) or the program selected steplessly or discretely. In this connection, reference is made to the WO 2007/107274, which is incorporated herein in its entirety for reference.

Because of manufacturing tolerances, the electric vibrational element 32 has a defined velocity at a specified operating voltage. Appreciable tolerances are present. In order to be able to set it definitively, the speed of the electric vibrational element 32 can be measured at a specified operating voltage and PWM triggering when starting up the wet razor and written in the EEPROM of the microprocessor (calibration of the micromotor speed). Alternatively, the actual speed can be measured by the microprocessor by means of the back EMF of the electric vibrational element 32 and an amplifier module for this signal. With that, a closed-loop control circuit can be set up in order to be able to set the micromotor speed at a defined value.

Additionally or alternatively, the function of changing the operating state can also be carried out automatically. Accordingly, it is possible to adapt the vibration frequency on the basis of the determined contacting force of the treatment head 12 or as a function of a measured supply voltage of the energy storage system 34. Advantageously, as the supply voltage decreases, the pulse duration or the vibration frequency of the electric vibrational element 32 is changed.

The inventive wet razor 10 moreover has an already mentioned charging state display function for the energy storage system 34. The charging state or the still remaining charging time can be displayed over the LCD display.

The user receives information from a timer or intermediate timer function concerning the duration of use already made or advice, for example, about a sufficient duration of use in a particular area of the face or, in the case of an electric toothbrush, in a particular quadrant of the teeth. Optical, acoustic or haptic signals can indicate to the user that a certain time has elapsed.

The method of producing the inventive wet razor 10 or a previously listed, analogously constructed wet razor with a correspondingly equipped treatment head 12 preferably takes place in a so-called multicomponent injection molding process. Initially, the basic body 22 with the appropriately shaped flexible zone 18 (bridge or film hinge) is molded from an already listed hard material. In addition, decorative parts, like, for example, the first shell part 24 shown in FIG. 14, the second shell part 26 and the window 28 are molded from a hard material and optionally decorated by means of the method already mentioned. The end cap 20 is also injection molded from a hard material and, if need be, coated with a soft material. Subsequently the already mentioned rear part of the negative supply contact is inserted in order to form the finished end cap 20.

In a next step, the shell parts 24, 26 with the window 28 and optionally further decorative parts are anchored to the basic body 22 or connected with the latter. Subsequently, the micromotor, used as the electric vibrating element 32, is inserted into the recess on the treatment head side and closed off with an appropriate lid 48.

The basic body 22, so completed, is subsequently inserted into an injection molding die and coated at least partially with soft material in order, by so doing, to fix the shell parts 24, 26, the window 28 and optionally further decorative parts permanently to the basic body 22 partially by means of over-molding. Optionally, the lid 48 for closing off the recess on the treatment head side, now occupied by the micromotor, is over-molded at least partly with a soft material in order to fix it to the basic body 22 and to close off the recess tightly. The flexible zone 18 is also completed with soft material by over-molding the basic body 22. By so doing, a mold core of the injection molding die which is inserted in the longitudinal direction of the handle 14 into the basic body 22, forms at least partially a boundary for the soft material of the flexible zone 18.

The cartridge-holding mechanism 16 which is preferably a separate sub-assembly is then inserted on the treatment head side and the component, already shown in FIG. 10 but without a battery and the rear part of the negative supply contact, is pushed into the recess of the handle 14 intended for this purpose.

For finishing the assembly of FIG. 10, the circuit boards 36 with the appropriate conducting parts is produced first and the electrical components affixed thereon by means of the already mentioned SMD the method. The FSI 56 and the snap-on disks 64 are also mounted on the circuit board 56. The second holding element 52 is also already connected with the front part of the negative supply contact of the energy storage system 14 and the LCD display with the already mentioned "zebra" is inserted into the first holding part 50. Furthermore, the circuit board 36 is snapped onto the first holding part 50 and the supply contacts of the energy supply system 34 are connected electrically with the appropriately provided contacts on the circuit board 36.

After the installation of the assembly shown in FIGS. 10 and 16, the electronic components, particularly the deflection sensor 54 and/or the electric vibrating element 32 are calibrated. For this purpose, a calibration pin, instead of an energy storage system 34, is inserted into the wet razor 10. The calibration pin has a defined operating voltage and contacts the two energy poles. In addition, the calibration pin is connected electrically with the EEPROM of the microprocessor. With a defined force on the treatment head 12, the values, measured by means of the deflection sensor 54, are stored in the EEPROM of the microprocessor. The same procedure is selected for calibrating the micromotor speed. However, the speed is determined with an external measuring device.

After the calibration, the energy storage system 34 is inserted into the recess of the handle 14 at the end region side and closed off tightly with the end cap 20. Optionally, an exchangeable razor cartridge is subsequently mounted on the cartridge holding mechanism 16 and the inventive wet razor is packaged in preparation for marketing.

As the inventive wet razor 10 has a microprocessor including RAM or flash memory and non-volatile memory, as previously described, it can store data, e.g. force data from the FSR related to expected or unexpected forces the razor experiences after calibration. Used razors, e.g. from tests conducted by the manufacturer, can have their memories interrogated to extract data related to the forces experienced by the razor. The information may be extracted from the memory based on the 'wired' or wireless communication technologies previously described. Furthermore, as the microprocessor includes a timer, the interrogation can correlate force with time. Preferably the microprocessor is programmed with a calendar and force events relative to time and date can be extracted. Alternatively the timer can start from 0 when the razor is calibrated. If a razor is interrogated and shows time=n then force event timing can be retrospectively calculated. Examples of resultant data that can be collected from the razor include: total number of shaves performed by the razor; maximum or average force sensed by the FSR; number of strokes per shave; average number of strokes per shave; average stroke duration; total "run" or use time of the razor; average run time per shave; average battery life; number of battery changes if a replaceable battery is used; number of button presses (e.g. for program changes); etc.

As already mentioned, all the properties, configurations, methods for production and functions described above may be used analogously also for other body care devices. The description of the inventive body care device 10 in the form of a wet razor is to be regarded as an example. Instead of razor cartridge(s), the treatment head 12 can be equipped in these cases with other attachments. By these means, electric toothbrushes with oscillating, swiveling or translatory bristle movement, vibrational brushes or sonic brushes, toothbrushes with combined movements of a cleaning element, or also manual toothbrushes with electrically produced additional functions (such as polishing force detection), mascara applicators for applying mascara, massage equipment, equipment for the removal of body hair, applicators for cosmetic products, etc., for example, can be equipped by these means. All properties, previously described, can be transferred analogously to these devices, without leaving the framework of the invention.

For the sake of completeness, a mascara applicator, consisting of a handle 14 and a treatment head 12, is also briefly described diagrammatically here. The representation is shown in FIGS. 18 and 19. In this connection, reference is made to US 2006/0032512, which is incorporated herein in its entirety for reference. The handle 14 preferably has a screw top in order to screw the mascara applicator onto the container with the mascara liquid or a fitting in order to slip the handle onto the container with the mascara liquid. The fitting 98 is shown in FIG. 19. The treatment head 12 consists of the mascara brush or applicator and a shaft 90. The mascara brush may be a screwed-in brush of individual, extruded bristles fixed with wire or a brush of bristles produced by injection molding. As in the case of the body care device 10, the vibrational element 32 is placed in the treatment head 12, preferably close by the mascara brush or under or in the mascara brush. With that, vibrations in the handle 14 that would be damped or absorbed by the hand of the user can preferably be avoided. The vibrating element 32 preferably consists of a micromotor with an eccentric mass 44 attached to a shaft of the motor. In addition to or as an alternative for the vibrating element 32, further main or subsidiary loads, described above, can be inserted in the shaft 90 or the handle 14. The diameter of the micromotor in this case is not more than 6 mm and preferably not more than 4 mm. The axis of the micromotor is parallel to the axis of the shaft 90. The shaft 90 is in one piece and hollow (not shown). Preferably, the hollow shaft 90 has different internal and external diameters and tapers in the direction of the mascara brush.

Alternatively, the shaft 90 is configured in several parts with different internal and external diameters, as shown, for example, in FIGS. 18 and 19. The part with the largest internal diameter accommodates the vibrational element 32. The parts of the shaft on the handle side and the brush side are also connected with this part; they are anchored preferably permanently (inserted, welded, glued, etc.).

The vibrational element 32 is positioned in the hollow shaft 90, as close as possible to the mascara brush. In any case, a tapered part of the shaft 90 is provided between the vibrational element 32 and the mascara brush. In the shaft 90, electrical leads 92 extend from the vibrational element 32 up to the circuit board 36. The electrical leads are permanently connected or soldered with the vibrational element 32 and the circuit board 36. The treatment head 12 with the mascara brush, the shaft 90 and the vibrational element 32 can also be deflected flexibly with respect to the handle 14. The flexible zone 18 is provided in the region of the anchorage of the shaft at the handle 14. In addition, a zone for damping vibrations, consisting, for example, of a soft material or a flexible structure, is also provided. With that, the vibrations, which are generated in the treatment head 12, are uncoupled from the handle 14. In order to avoid repetitions, a detailed description of the flexible zone 18 and of the implementation of the deflection sensor 54 is omitted here. Nevertheless, an actuating extension 74, which is carried on a deflection sensor 54, is shown in the Figure by way of example. This arrangement is to be understood as being similar to the arrangement in the case of the body care device 10. Since the treatment head 12 for the mascara brushes or applicators preferably is rotationally symmetrical or at least approximately rotationally symmetrical, such a sensor in the handle 14 must also act radially. This can be achieved with a sensor of appropriate shape or with the installation of several sensors.

The energy storage system 34, in the form of a button battery with a voltage preferably of 1.5 V, is fixed on the circuit board 36 in a holding element 52, which preferably is exchangeable and not shown. The electrical components, disposed on the circuit board 36, are connected electrically with zones, surface zone 94 and surface zone 96, on the surface of the handle 14. As discussed above, these surface zones 94 and 95 consist of electrically conducting material, such as an electrically conducting plastic, preferably an electrically conducting hard material, which connects during the injection molding with the hard material of the basic body (material fusion during the multi-component injection molding), an electrically conducting paint or metallic or metal surfaces. The electrically conducting surface zones, 94 and 95 are connected with the circuit board 36 and, furthermore, with the microprocessor or other electrical components and the vibrating element 32 are switched on when the two surface zones are connected, for example, by contact. At the same time, a change in the electric current the resistance the voltage or the capacitance is used as a measurement parameter.

At its free end region, the handle 14 has a wheel 100 for adjusting the frequency of the vibration or for selecting a program. The wheel 100 is connected mechanically and/or electrically with the circuit board 36. In this connection, reference is made to WO 2007/107274, previously mentioned.

The elements for putting out information, such as the LCD, LED, or loudspeaker etc., are integrated as in the case of the body care device 10. The treatment head 12 with the whole of the electronic functional unit 30 preferably is installed at the front in the handle (mechanically anchored by means of snaps, screws, etc.).

Figure 20:
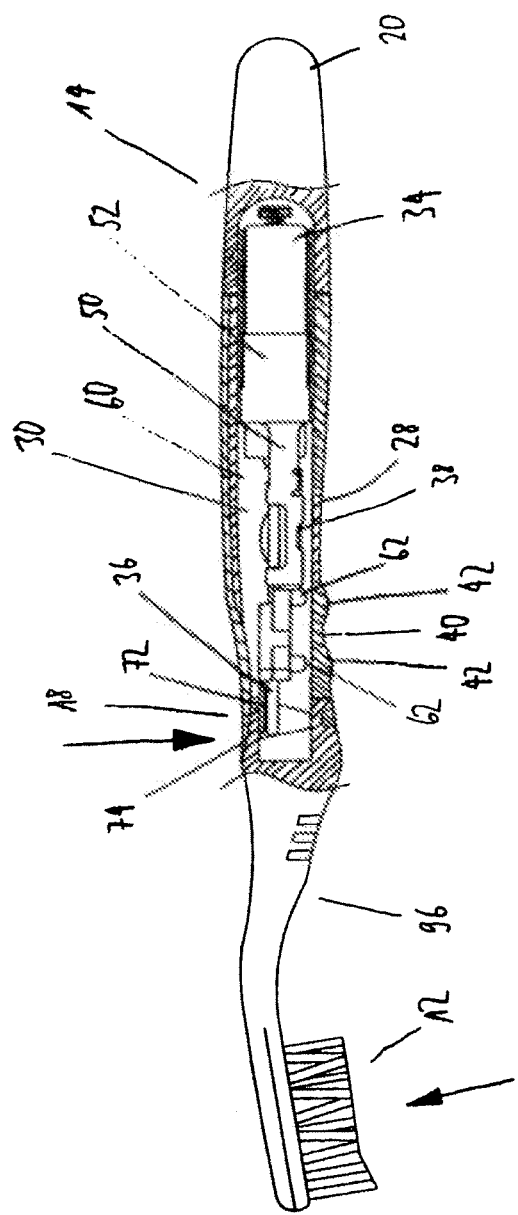
FIG. 20 shows an example of the application of the invention in a toothbrush in a longitudinal sectional representation.

In FIG. 20, a toothbrush is shown, the essential features of which are based directly on that of the body care device 10 in the form of a wet razor. All the functions of the body care device 10 in the form of a wet razor, which have been described, can also be employed for toothbrushes. FIG. 20 shows a manual toothbrush, which is equipped, for example, with a force monitor, although, as already described, electric toothbrushes of every kind can be adapted with the functions herein described. For example, a vibrational element 32 in the form of a micromotor with an eccentric weight could be installed in the neck portion 96.

The toothbrush consists of a handle 14, which is equipped at least partly with a handle recess 60, the neck part 96 and the treatment head 12. When the brush is in use, the treatment head 12 is placed under force as indicated by the arrows. This force is passed on further to the flexible zone 18. The flexible zone 18 makes it possible to deflect the treatment head 12 elastically with respect to the handle 14. At the same time, the actuating extension 74 is pressed on to the force elements 70, which actuates the deflection sensor 54 and acts on the force-sensitive resistance 56. The difference from the arrangement of the body care device 10 in the present embodiment consists therein that the switching membrane 40 with the switching elements 42 is mounted on the action side of the treatment head 12; as a result, the electrical components of the electrical functional unit 32 are partly rotated. Of course, such an arrangement of the switching elements is also possible in the case of the body care device 10. For this reason, the key elements 62, for example, are now disposed on the action side and likewise, the window 28 with the view of the display unit 38 is also disposed on the action side. The circuit board 36 with the different electrical components is connected by means of the holding element 50 with the holding element 52 and, accordingly, with the energy storage unit 34. The end cap 20 of the toothbrush 10 is also shown, the transition between the end cap 20 and the hollow space not being shown in detail.

The user interface of the toothbrush and the razor can be designed alternatively as a touch screen. The switching elements 42 are directly integrated and also the display unit 38 would be replaced by the touch screen. The covering material of the touch screen means the window 28 and also the material of the switching elements needs to be adjusted to the touch screen. Alternatively the touch screen is directly mounted, without protective cover, on the surface of the appliance.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. For instance, features disclosed in connection with any one embodiment can be used alone or in combination with each feature of the respective other embodiments. It is clearly understood that all embodiments shown or described in the shape of a particular body care product for instance as a wet razor may also be generally applicable to other body care products such as toothbrushes or a mascara applicators.

The invention claimed is:

1. A body care device comprising:
a base body having a handle, a treatment head, the treatment head being connected with the handle via a flexible zone, the flexible zone enabling an elastic deflection of the treatment head with respect to the handle during use of the body care device, a deflection sensor, the deflection sensor being connected to an electrical circuit,
wherein the deflection sensor generates an electrical signal as a function of the elastic deflection, and
wherein the flexible zone includes an actuating extension molded from a material, and when the flexible zone is elastically deflected by a force exerted thereupon, an opposing force is exerted by the actuating extension on the deflection sensor.

2. The body care device of claim 1, wherein the flexible zone is formed adjacent a region of a hollow cavity of the handle for accommodating an electrical functional unit.

3. The body care device of claim 2, wherein the base body further includes a window which enables visual information to be exchanged from a display unit, disposed in an interior of the base body, to a user.

4. The body care device of claim 1, wherein the deflection sensor is one of an FSR, a piezoelectric resistance or a strain gauge and the deflection sensor has a force-sensitive, pressure- sensitive or extension-sensitive resistance.

5. The body care device of claim 1, further comprising a force element disposed between the actuating extension and the deflection sensor.

6. The body care device of claim 5, wherein the force element is plate-shaped.

7. The body care device of claim 1, further comprising an electrically drivable vibrating element adapted to produce vibrations at the treatment head, wherein, upon the deflection of the treatment head above a specified threshold value, the vibrating element is automatically switched into an active operating state.

8. The body care device of claim 7, wherein an operating state of the vibrating element is capable of being automatically controlled by the elastic deflection of the treatment head.

9. The body care device of claim 7, wherein during the deflection of the treatment head below a specified threshold value, the vibrating element is capable of being switched into a deactivated operating state.

10. The body care device of claim 7, further comprising a counting unit adapted to count a number of active operating states as a function of a duration of each state, determined by virtue of a timer unit.

11. The body care device of claim 7, further comprising a pulse width modulation unit, which can be used for the electrical triggering of the vibrating element, which is capable of acoustic or haptic signaling to the user.

12. The body care device of claim 1, further comprising electrical components for an optical display and/or for an acoustic signaling, and/or for heating or cooling, and/or for supplying electric energy.

13. The body care device of claim 1, further comprising a microprocessor for processing signals of the sensor of the body care device, and for programmable output of electrical signals for controlling electrical or further electrical components of the body care device.

14. The body care device of claim 13, wherein the body care device comprises means of communication with an external processor.

15. The body care device of claim 14, wherein the communication means are wire-based means, and whereby the communication means is provided with a removable, water-proof seal or cover.

16. The body care device of claim 14, wherein the communication means are wireless means.

17. The body care device of claim 1, wherein the body care device comprises a microprocessor, which controls display functions, output signals, loads, a driving device, a loudspeaker or electrical components for an optical display and/or for an acoustic signaling, and/or for heating or cooling, and/or for supplying electric energy, and which processes and/or stores signals of the sensor.

18. The body care device of claim 17, wherein data stored in a memory of the microprocessor is transferable by a communication means to an external processor.

19. The body care device of claim 1, wherein the device is a wet razor and the treatment head is adapted for carrying a razor cartridge.

20. The body care device of claim 1, wherein the body care device is a wet razor, a toothbrush or a mascara applicator.

21. The body care device of claim 1, wherein the flexible zone comprises a portion of a material integrally formed with the handle and the treatment head.

22. The body care device of claim 21, wherein the base body has at least one recess on a side of the flexible zone portion, the at least one recess being at least partially filled with a second material.

23. The body care device of claim 21, wherein the flexible zone is produced by means of a multi-component injection molding method and the second material in the at least one recess is limited by means of a mold core introduced into the base body in a longitudinal direction of the handle.

* * * * *